US009216181B2

(12) United States Patent
Rossini

(10) Patent No.: US 9,216,181 B2
(45) Date of Patent: Dec. 22, 2015

(54) BMP-2 UPREGULATING COMPOUNDS FOR HEALING BONE TISSUE AND SCREENING METHODS FOR SELECTING SUCH COMPOUNDS

(71) Applicant: Southwest Research Institute, San Antonio, TX (US)

(72) Inventor: Jorge Gianny Rossini, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 130 days.

(21) Appl. No.: 13/896,993

(22) Filed: May 17, 2013

(65) Prior Publication Data

US 2013/0252947 A1 Sep. 26, 2013

Related U.S. Application Data

(63) Continuation-in-part of application No. 13/156,089, filed on Jun. 8, 2011.

(51) Int. Cl.

| | |
|---|---|
| ***A61K 31/435*** | (2006.01) |
| ***A61K 31/44*** | (2006.01) |
| ***A61K 38/18*** | (2006.01) |
| ***A61P 19/08*** | (2006.01) |
| ***A61K 31/5415*** | (2006.01) |
| ***A61K 31/445*** | (2006.01) |
| ***A61K 31/454*** | (2006.01) |
| ***A61K 45/06*** | (2006.01) |
| ***A61K 38/22*** | (2006.01) |
| ***A61K 31/472*** | (2006.01) |
| ***A61K 31/517*** | (2006.01) |
| ***A61K 31/4402*** | (2006.01) |
| ***A61K 31/573*** | (2006.01) |

(52) U.S. Cl.

CPC ............. *A61K 31/5415* (2013.01); *A61K 31/44* (2013.01); *A61K 31/4402* (2013.01); *A61K 31/445* (2013.01); *A61K 31/454* (2013.01); *A61K 31/472* (2013.01); *A61K 31/517* (2013.01); *A61K 31/573* (2013.01); *A61K 38/18* (2013.01); *A61K 38/22* (2013.01); *A61K 45/06* (2013.01)

(58) Field of Classification Search

CPC . A61K 2300/00; A61K 45/06; A61K 31/366; A61K 31/00; A61K 38/1875; A61K 31/47; A61K 31/517; A61K 31/54

See application file for complete search history.

(56) References Cited

U.S. PATENT DOCUMENTS

| | | | | |
|---|---|---|---|---|
| 4,256,743 | A * | 3/1981 | Goldhaber | 514/226.2 |
| 5,478,837 | A | 12/1995 | Rodgers et al. | |
| 5,631,142 | A | 5/1997 | Wang et al. | |
| 6,071,530 | A | 6/2000 | Polson et al. | |
| 6,083,690 | A | 7/2000 | Harris et al. | |
| 6,150,328 | A * | 11/2000 | Wang et al. | 514/8.8 |
| 6,902,721 | B1 | 6/2005 | Mundy et al. | |
| 7,087,225 | B2 | 8/2006 | Yu et al. | |
| 7,223,554 | B2 | 5/2007 | Garrett et al. | |
| 7,638,486 | B2 | 12/2009 | Lazarov et al. | |
| 7,829,535 | B2 | 11/2010 | O'Connor | |
| 2004/0186184 | A1* | 9/2004 | Berlin | 514/649 |
| 2008/0280826 | A1 | 11/2008 | O'Connor | |
| 2010/0285087 | A1 | 11/2010 | McDonough et al. | |
| 2012/0316111 | A1 | 12/2012 | Rossini | |

FOREIGN PATENT DOCUMENTS

| | | | |
|---|---|---|---|
| WO | 9011366 | A1 | 10/1990 |
| WO | 9203125 | A1 | 3/1992 |
| WO | 9320859 | A1 | 10/1993 |

OTHER PUBLICATIONS

Hardcastle et al., J. Physiol., 1987, vol. 388:521-532.*

Bangham, et al., "Diffusion of Univalent Ions across the Lamellae of Swollen Phospholipids," J Mol Biol. Aug. 1965;13(1):238-52.

Beck, et al, "Rapid Publication TGF-β1 Induces Bone Closure of Skull Defects," Journal of Bone and Mineral Research (1991) vol. 6, Issue: 11, pp. 753-761.

Caplan, et al., "Mesenchymal Stem Cells," Journal of Orthopaedic Research vol. 9, Issue 5, pp. 641-650, Sep. 1991.

Chen et al., "Bone Morphogenetic Protein 2 (BMP-2) Enhances BMP-3, BMP-4, and Bone Cell Differentiation Marker Gene Expression During the Induction of Mineralized Bone Matrix Formation in Cultures of Fetal Rat Calvarial Osteoblasts," Calcified Tissue International, vol. 60, No. 3, 283-290 (1997).

Chen, et al., "Differential roles for bone morphogenetic protein (BMP) receptor type IB and IA in differentiation and specification of mesenchymal precursor cells to osteoblast and adipocyte lineages.," J Cell Biol. Jul. 13, 1998;142 (1):295-305.

Dalby, et al., "The control of human mesenchymal cell differentiation using nanoscale symmetry and disorder," Nature Materials 6, 997-1003 (2007).

Edelman, et al., "Controlled and modulated release of basic fibroblast growth factor," Biomaterials. Sep. 1991;12 (7):619-26.

Garrett, et al., "Selective inhibitors of the osteoblast proteasome stimulate bone formation in vivo and in vitro," J Clin Invest. Jun. 2003;111(11):1771-82.

Harris, et al., "Recombinant Bone Morphogenetic Protien 2 Accelerates Bone Cell Differentiation and Stimulates BMP-2 Promoter Activity in Primary Fetal Rat Calvarial Osteoblast Cultures," Mol. and Cell. Diff. 3(2): 137-155 (1995).

Kim, et al., "Preparation of Multivesicular Liposomes," Biochim Biophys Acta. Mar. 9, 1983;728(3):339-48.

Ksander, et al., "Exogenous Transforming Growth Factor-Beta 2 Enhances Connective Tissue Formation and Wound Strength in Guinea Pig Dermal Wounds Healing by Secondary Intent," Ann Surg. Mar. 1990;211(3):288-94.

(Continued)

*Primary Examiner* — Xiaozhen Xie

(74) *Attorney, Agent, or Firm* — Grossman, Tucker et al.

(57) ABSTRACT

The present disclosure relates to a method to stimulate endogenous BMP-2 up-regulation in a subject which method comprises administering to a subject an effective amount of an H1 receptor antagonist, whereby endogenous BMP-2 up-regulation is stimulated in said subject. Also provided is a pharmaceutical formulation including an H1 receptor antagonist present in an effective amount to stimulate BMP-2 up-regulation in a subject and a kit.

7 Claims, 40 Drawing Sheets
(35 of 40 Drawing Sheet(s) Filed in Color)

(56) References Cited

OTHER PUBLICATIONS

Lee, et al., "Fluvastatin and Lovastatin but not Pravastatin Induce Neurologial Differentiation in Human Mesenchymal Stem Cells," J Cell Biochem. Nov. 15, 2004;93(5):917-28.
Mayer, et al., "Vesicles of variable sizes produced by a rapid extrusion procedure," Biochim Biophys Acta. Jun. 13, 1986;858(1):161-8.
Mundy, et al., "Stimulation of Bone Formation in Vitro and in Rodents by Statins," Science Dec. 3, 1999: vol. 286 No. 5446 pp. 1946-1949.
Murray, et al., "The ubiquitin-proteasome system and cellular proliferation and regulation in osteoblastic cells," Exp Cell Res Aug. 1, 1998;242(2):460-9.
Olson, et al., "Preparation of Liposomes of Defines Size Distribution by Extrusion Through Polycarbonate Membranes," Biochim Biophys Acta. Oct. 19, 1979;557(1):9-23.
Raimondo, et al., "Morphological characterization of GFP transfected adult mesenchymal bone marrow stem cells," J Anat. Jan. 2006;208(1):3-12.
Shea, et al., "BMP Treatment of C3H10T1/2 Mesenchymal Stem Cells Induces Both Chondrogenesis and Osteogenesis," J Cell Biochem. Dec. 15, 2003;90(6):1112-27.
Szoka, Jr., et al., "Procedure for preparation of liposomes with large internal aqueous space and high capture by reverse-phase evaporation," Proc. Natl. Acad. Sci. USA, vol. 75, No. 9, pp. 4194-4198, Sep. 1978 Biochemistry.
Drug Information Online Quinacrine <<http://www.drugs.com/cons/quinacrine-systemic.html>>)(Jul. 29, 2002) (3 pgs) Office Actions with mail dates Nov. 5, 2013 and Sep. 16, 2014 in related U.S. Appl. No. 13/156,089.

* cited by examiner

BMP-2 UPREGULATING COMPOUNDS FOR HEALING BONE TISSUE AND SCREENING METHODS FOR SELECTING SUCH COMPOUNDS

CROSS-REFERENCE TO RELATED APPLICATIONS

The present application is a continuation-in-part of U.S. application Ser. No. 13/156,089, filed on Jun. 8, 2011, the teachings of which are incorporated herein by reference.

FIELD

The present application relates to the use of $H_1$ receptor antagonists as BMP-2 up-regulating compounds for healing bone tissue and, in particular, the use of terfenadine, promethazine, astemizole, carebastine, ebastine and pheniramine as BMP-2 up-regulating compounds for healing bone tissue.

BACKGROUND

Bone may be subject to constant breakdown and resynthesis in a complex process mediated by osteoblasts, which produce new bone, and osteoclasts, which destroy bone. The activities of these cells are regulated by a large number of cytokines and growth factors, many of which have now been identified and cloned.

A number of conditions are characterized according to the need to enhance bone formation or to inhibit bone resorption. Examples in which the enhancement of bone formation may be found beneficial include, but are not limited to, bone fractures, medical procedures where bone is altered, or various forms of osteoporosis, where it may be desirable to stimulate bone growth and to aid in bone repair. Treatment these various bone conditions or other skeletal disorders, such as those associated with cartilage, may be achieved by enhancing bone formation and/or inhibiting bone resorption.

BMP-2 has been recognized as a growth factor that can control stem cell differentiation during tissue regeneration. This endogenous factor may be produced by the body during bone tissue regeneration during fracture healing, such as in disease states including osteoporosis. Sometimes, however, the amount of the endogenous factor produced by the human body may not be sufficient, which may lead to deficiencies.

Recombinant material has been utilized to supplement the deficiency of the endogenous factor. Application of such materials may be useful, not only for bone fractures, but for other regenerative conditions such as degenerative diseases involving joint cartilage, neurons and kidney. However, recombinant materials may be relatively expensive and my exhibit relatively lower efficiency compared to endogenously produced BMP-2.

SUMMARY

In one aspect, the present disclosure relates to a method to stimulate endogenous BMP-2 up-regulation in a subject which method comprises administering to a subject an effective amount of an $H_1$ receptor antagonist, whereby endogenous BMP-2 up-regulation is stimulated in said subject.

In another aspect, the present disclosure also relates to a pharmaceutical formulation for the delivery of an endogenous BMP-2 up-regulator, comprising an $H_1$ receptor antagonist present in an effective amount to stimulate BMP-2 up-regulation in a subject.

In a further aspect, the present disclosure also relates to a kit comprising a vessel containing a composition including from 0.02 mg/kg to 1,000 mg/kg an $H_1$ receptor antagonist and instructions for the administration of the $H_1$ receptor antagonist to a subject.

BRIEF DESCRIPTION OF DRAWINGS

The above-mentioned and other features of this disclosure, and the manner of attaining them, may become more apparent and better understood by reference to the following description of embodiments described herein taken in conjunction with the accompanying drawings, wherein.

Figure 1:
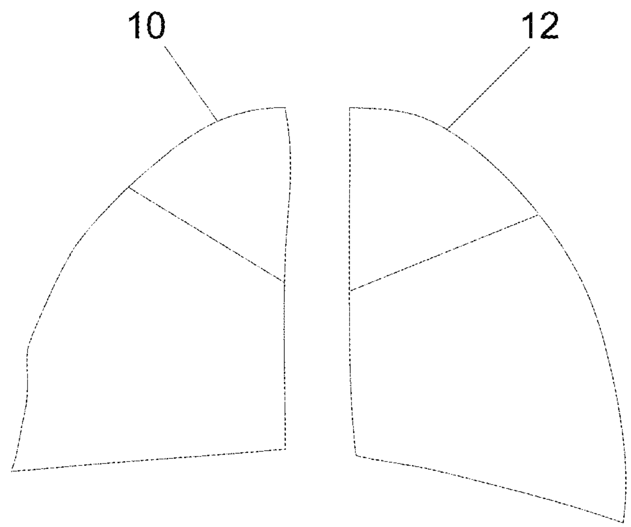
FIG. 1 provides an illustration of an example of murine calvaria removed from 4 day old pups.

The patent application file contains at least one drawing executed in color. Copies of this patent application publication with color drawings will be provided by the Office upon request and payment of the necessary fee.

DETAILED DESCRIPTION

The present disclosure relates to a method of using bone morphogenetic protein-2 (BMP-2) up-regulating compounds for stimulating endogenous BMP-2 gene expression to aid in healing bone tissue. The identified BMP-2 up-regulators may be utilized in various bone orthopedic applications including, for example, the healing of bone fractures, use as bone fillers, spinal fusion, as well as dental applications to induce new alveolar bone. Bone morphogenetic proteins, including BMP-2, are understood to belong to the transforming growth factor beta (TGF-β) superfamily of proteins, which generally include proteins that control proliferation, cellular differentiation and other functions. BMP-2, in particular, is understood to play a roll in the development of bone and cartilage and in particular, osteoblast differentiation has been found to be enhanced by BMP-2. (S. E. Harris, et al., Mol. Cell Diff. 3, 137 (1995); D. Chen, et al., Calcif. Tissue Int. 60, 283 (1997)).

Thus, provided herein are methods of treating bone defects (including osteoporosis, bone fractures, osteolytic lesions, metastic bone disease, post-plastic surgery healing, and segmental bone defects) in subjects suffering therefrom. The method comprises administering to a subject an $H_1$ receptor antagonist; and preferably, one or more of the following: a first generation $H_1$ receptor antagonist and a second generation $H_1$ receptor antagonists; and more preferably, one or more of the following compounds: terfenadine, ebastine, carebastine, pheniramine, astemizole and promethazine, in an amount sufficient to stimulate endogenous BMP-2 up-regulation. It is noted that carebastine is an active metabolite of ebastine, transformed by the liver. It has been found herein that these receptor antagonists stimulate endogenous BMP-2 up-regulation.

$H_1$ receptor antagonists may be understood as a pharmaceutical drug that inhibits the action of histamine by blocking it from attaching to histamine receptors. First generation $H_1$ receptor antagonists contain aromatic rings and alkyl substitutions and are relatively lipophilic. They traditionally bind to the $H_1$-receptor and prevent histamine interactions with the receptor. $H_1$ receptor antagonists typically exhibit the following general chemical formula:

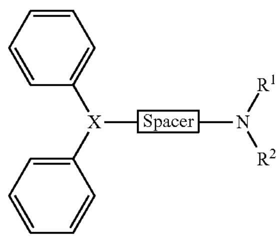

In the above formula, X may be N, C or CO and R1 and R2 may be relatively small alkyl groups including 1 to 8 carbon atoms. The spacer may be 2-3 carbon atoms in length, linear, cyclic, branches, saturated or unsaturated.

Second generation $H_1$ receptor antagonists exhibit relatively lower lipid solubility characteristics than their first generation counterparts and are generally more selective than their first generation counterparts.

As employed herein, the term "subject" may be understood to include human as well as other non-human vertebrate animal species, such as, for example, canine, feline, bovine, porcine, rodent, ayes and the like. It will be understood by the skilled practitioner that the subject is one appropriate to the desirability of stimulating bone growth. Thus, in general, for example, healing of bone tissue will be confined in most instances to animals that would appropriately exhibit such healing.

As used herein, "treat" or "treatment" may include a postponement of development of bone deficit symptoms and/or a reduction in the severity of such symptoms that will or may be expected to develop. These terms may further include ameliorating existing bone or cartilage deficit symptoms, preventing additional symptoms, ameliorating or preventing the underlying metabolic causes of symptoms, and/or encouraging bone growth. Thus, the terms may denote that a beneficial result has been conferred on a vertebrate subject with a cartilage, bone or skeletal deficit, or with the potential to develop such deficit.

"Bone deficit" may be understood as an imbalance in the ratio of bone formation to bone resorption, such that, if unmodified, the subject will exhibit less bone than desirable, or the subject's bones will be less intact and coherent than desired. Bone deficit may also result from fracture, from surgical intervention or from dental or periodontal disease. By "cartilage defect" it may be understood as damaged cartilage, less cartilage than desired, or cartilage that is less intact and coherent than desired. "Bone disorders" may include both bone deficits and cartilage defects.

Representative uses of the compounds identified by the screening methods and assays described herein may include: repair of bone defects and deficiencies, such as those occurring in closed, open and non-union fractures; prophylactic use in closed and open fracture reduction; promotion of bone healing in plastic surgery; stimulation of bone in-growth into non-cemented prosthetic joints and dental implants; elevation of peak bone mass in pre-menopausal women; treatment of growth deficiencies; treatment of periodontal disease and defects, and other tooth repair processes; increase in bone formation during distraction osteogenesis; and treatment of other skeletal disorders, such as age-related osteoporosis, post-menopausal osteoporosis, glucocorticoid-induced osteoporosis or disuse osteoporosis and arthritis, or any condition that benefits from stimulation of bone formation. The compounds described herein can also be useful in repair of congenital, trauma-induced or surgical resection of bone (for instance, for cancer treatment), and in cosmetic surgery. Further, the compounds described herein may be used for limiting or treating cartilage defects or disorders, and may be useful in wound healing or tissue repair.

The compositions for up-regulation of BMP-2 described herein may be administered systemically or locally. For systemic use, the compounds herein may be formulated for parenteral (e.g., intravenous, subcutaneous, intramuscular, intraperitoneal, intranasal or transdermal) or enteral (e.g., oral or rectal) delivery according to conventional methods. Intravenous administration can be by a series of injections or by continuous infusion over an extended period. Administration by injection or other routes of discretely spaced administration can be performed at intervals ranging from weekly to once to three times daily. Alternatively, the compounds disclosed herein may be administered in a cyclical manner (administration of disclosed compound; followed by no administration; followed by administration of disclosed compound, and the like). Treatment may continue until the desired outcome is achieved.

In general, pharmaceutical formulations may include a compound for up-regulation of BMP-2 identified herein in combination with a pharmaceutically acceptable vehicle, such as saline, buffered saline, 5% dextrose in water, borate-buffered saline containing trace metals or the like. Formulations may further include one or more excipients, preservatives, solubilizers, buffering agents, albumin to prevent protein loss on vial surfaces, lubricants, fillers, stabilizers, etc. Methods of formulation are well known in the art and are disclosed, for example, in Remington's Pharmaceutical Sciences, latest edition, Mack Publishing Co., Easton Pa., which is incorporated herein by reference. Pharmaceutical compositions may be in the form of sterile, non-pyrogenic liquid solutions or suspensions, coated capsules, suppositories, lyophilized powders, transdermal patches or other forms known in the art. Local administration may be by injection at the site of injury or defect, or by insertion or attachment of a solid carrier at the site, or by direct, topical application of a viscous liquid, or the like. For local administration, the delivery vehicle preferably provides a matrix for the growing bone or cartilage, and more preferably may be a vehicle that can be absorbed by the subject without adverse effects.

Delivery of compounds herein to wound sites may be enhanced by the use of controlled-release compositions, such as those described in PCT publication WO93/20859, which is incorporated herein by reference. Films of this type may be particularly useful as coatings for prosthetic devices and surgical implants. The films may, for example, be wrapped around the outer surfaces of surgical screws, rods, pins, plates and the like. Implantable devices of this type are understood to be routinely used in orthopedic surgery. The films can also be used to coat bone filling materials, such as hydroxyapatite blocks, demineralized bone matrix plugs, collagen matrices and the like. In general, a film or device as described herein may be applied to the bone at the fracture or defect site. Application may be generally performed by implantation into the bone or attachment to the surface using standard surgical procedures.

In addition to the copolymers and carriers noted above, the biodegradable films and matrices may include other active or inert components. Of particular interest are those agents that are understood to promote bone and/or cartilage tissue growth or infiltration, such as additional growth factors. Exemplary growth factors may include epidermal growth factor (EGF), fibroblast growth factor (FGF), platelet-derived growth factor (PDGF), transforming growth factors (TGFs), parathyroid hormone (PTH), leukemia inhibitory factor (LIF), insulin-like growth factors (IGFs) and the like. Agents that promote bone growth, such as bone morphogenetic proteins including BMP-7 and/or BMP-2, and NaF, may also be utilized. Biodegradable films or matrices may include calcium sulfate, tricalcium phosphate, hydroxyapatite, polylactic acid, polyanhydrides, bone or dermal collagen, pure proteins, extracellular matrix components and the like and combinations thereof. Such biodegradable materials may be used in combination with non-biodegradable materials, to provide desired mechanical, cosmetic or tissue or matrix interface properties.

Alternative methods for delivery of compounds described herein may include use of ALZET osmotic minipumps (Alza Corp., Palo Alto, Calif.); sustained release matrix materials such as those disclosed in Wang, et al. (PCT Publication WO90/11366); electrically charged dextran beads, as disclosed in Bao, et al. (PCT Publication WO92/03125); collagen-based delivery systems, for example, as disclosed in Ksander, et al., Ann. Surg. (1990) 211(3):288 294; methylcellulose gel systems, as disclosed in Beck, et al., J Bone Min. Res. (1991) 6(11):1257 1265; alginate-based systems, as disclosed in Edelman, et al., Biomaterials (1991) 12:619 626 and the like. Other methods well known in the art for sustained local delivery in bone may include porous coated metal prostheses that can be impregnated and solid plastic rods with therapeutic compositions incorporated within them.

The compounds identified herein may also be used in conjunction with agents that inhibit bone resorption. Antiresorptive agents, may include, but are not limited to estrogen, bisphosphonates and calcitonin. More specifically, the compounds disclosed herein may be administered for a period of time (for instance, days to weeks, weeks to months or months to years) sufficient to obtain correction of a bone deficit condition. Once the bone deficit condition has been corrected, the vertebrate can be administered an anti-resorptive compound to maintain the corrected bone condition. Alternatively, the compounds disclosed herein may be administered with an anti-resorptive compound in a cyclical manner (administration of disclosed compound, followed by anti-resorptive, followed by disclosed compound, and the like).

In additional formulations, conventional preparations such as those described below may be used.

Aqueous suspensions may contain the active ingredient in admixture with pharmacologically acceptable excipients, comprising suspending agents, such as methyl cellulose; and wetting agents, such as lecithin, lysolecithin or long-chain fatty alcohols. The aqueous suspensions may also contain preservatives, coloring agents, flavoring agents, sweetening agents and the like in accordance with industry standards.

Preparations for topical and local application may include aerosol sprays, lotions, gels and ointments in pharmaceutically appropriate vehicles which vehicles may include lower aliphatic alcohols, polyglycols such as glycerol, polyethylene glycol, esters of fatty acids, oils and fats, and silicones. The preparations may further include antioxidants, such as ascorbic acid or tocopherol, and preservatives, such as p-hydroxybenzoic acid esters. Parenteral preparations may include particularly sterile or sterilized products. Injectable compositions may be provided containing the active compound and any of the well known injectable carriers. These may contain salts for regulating the osmotic pressure.

If desired, the osteogenic agents can be incorporated into liposomes by any of the reported methods of preparing liposomes for use in treating various pathogenic conditions. The present compositions may utilize the compounds noted above incorporated in liposomes in order to direct these compounds to macrophages, monocytes, as well as other cells and tissues and organs which take up the liposomal composition. The liposome-incorporated compounds may be utilized by parenteral administration, to allow for the efficacious use of lower doses of the compounds. Ligands may also be incorporated to further focus the specificity of the liposomes.

Suitable conventional methods of liposome preparation may include, but are not limited to, those disclosed by Bangham, A. D., et al., J Mol Biol (1965) 23:238 252, Olson, F., et al., Biochim Biophys Acta (1979) 557:9 23, Szoka, F., et al., Proc Natl Acad Sci USA (1978) 75:4194 4198, Kim, S., et al., Biochim Biophys Acta (1983) 728:339 348, and Mayer, et al., Biochim Biophys Acta (1986) 858:161 168.

The liposomes may be made from the present compounds in combination with any of the conventional synthetic or natural phospholipid liposome materials including phospholipids from natural sources such as egg, plant or animal sources such as phosphatidyicholine, phosphatidylethanolamine, phosphatidylglycerol, sphingomyelin, phosphatidylserine, or phosphatidylinositol and the like. Synthetic phospholipids that may also be used, include, but are not limited to: dimyristoylphosphatidylcholine, dioleoylphosphatidylcholine, dipalmitoylphosphatidylcholine and distearoylphosphatidycholine, and the corresponding synthetic phosphatidylethanolamines and phosphatidylglycerols. Cholesterol or other sterols, cholesterol hemisuccinate, glycolipids, cerebrosides, fatty acids, gangliosides, sphingolipids, 1,2-bis(oleoyloxy)-3-(trimethyl ammonio) propane (DOTAP), N-[1-(2,3-dioleoyl) propyl-N,N,N-trimethylammonium chloride (DOTMA), and other cationic lipids may be incorporated into the liposomes, as is known to those skilled in the art. The relative amounts of phospholipid and additives used in the liposomes may be varied if desired. The preferred ranges are from about 60 to 90 mole percent of the phospholipid; cholesterol, cholesterol hemisuccinate, fatty acids or cationic lipids may be used in amounts ranging from 0 to 50 mole percent. The amounts of the present compounds incorporated into the lipid layer of liposomes can be varied with the concentration of the lipids ranging from about 0.01 to about 50 mole percent.

Veterinary uses of the disclosed compounds may also be contemplated, as set forth above. Such uses would include treatment of bone or cartilage deficits in domestic animals, livestock and thoroughbred horses.

In embodiments, the compounds identified herein may be used to stimulate growth of bone-forming cells or their precursors, or to induce differentiation of bone-forming cell precursors, either in vitro or ex vivo. As used herein, the term "precursor cell" refers to a cell that is committed to a differentiation pathway, but that generally does not express markers or function as a mature, fully differentiated cell. As used herein, the term "mesenchymal cells" or "mesenchymal stem cells" refers to pluripotent progenitor cells that are capable of dividing many times, and whose progeny will give rise to skeletal tissues, including cartilage, bone, tendon, ligament, marrow stroma and connective tissue (see A. Caplan, J Orthop. Res. (1991) 9:641 650). As used herein, the term "osteogenic cells" includes osteoblasts and osteoblast precursor cells (or pre-osteoblasts) and the term "chondrogenic cells" includes chondroblasts and chondroblast precursor cells (or pre-chondroblasts). More particularly, the disclosed compounds may be useful for stimulating a cell population containing mesenchymal cells, thereby increasing the number of osteogenic and/or chondrogenic cells in that cell population. In a preferred method, hematopoietic cells may be removed from the cell population, either before or after stimulation with the disclosed compounds. Through practice of such methods, osteogenic and/or chondrogenic cells may be expanded. The expanded osteogenic cells can be infused (or reinfused) into a vertebrate subject in need thereof. For instance, a subject's own mesenchymal stem cells can be exposed to compounds described herein ex vivo, and the resultant osteogenic cells could be infused or directed to a desired site within the subject, where further proliferation and/or differentiation of the osteogenic cells can occur without immunorejection. Alternatively, the cell population exposed to the disclosed compounds may be immortalized human fetal osteoblastic or osteogenic cells. If such cells are infused or implanted in a vertebrate subject, it may be advantageous to "immunoprotect" these non-self cells, or to immunosuppress (preferably locally) the recipient to enhance transplantation and bone or cartilage repair.

An "effective amount" of a composition may be understood as that amount which produces an observable up-regulation of BMP-2 gene expression, which may be detected visually or through PCR (in some embodiments, exhibiting 2 fold or more, and preferably 3 fold or more, may positively indicate BMP-2 upregulation). For example, an "effective amount" for therapeutic uses is the amount of the composition comprising an active compound herein required to provide an increase in healing rates over healing rates observed when the compound is not present in fracture repair; reversal of bone loss in osteoporosis; reversal of cartilage defects or disorders; prevention or delay of onset of osteoporosis; stimulation and/or augmentation of bone formation in fracture non-unions and distraction osteogenesis; increase and/or acceleration of bone growth into prosthetic devices; and repair of dental defects. Such effective amounts will be determined using routine optimization techniques and are dependent on the particular condition to be treated, the condition of the patient, the route of administration, the formulation, and the judgment of the practitioner and other factors evident to those skilled in the art. The dosage required for the compounds identified herein (for example, in osteoporosis where an increase in bone formation is desired) is manifested as an increase in bone mass between treatment and control groups. This difference in bone mass may be seen, for example, as a 5-20% or more increase in bone mass in the treatment group. Other measurements of an increase in healing may include, for example, tests for breaking strength and tension, breaking strength and torsion, 4-point bending, increased connectivity in bone biopsies and other biomechanical tests well known to those skilled in the art. General guidance for treatment regimens is obtained from experiments carried out in animal models of the disease of interest.

The dosage of the compounds described herein will vary according to the extent and severity of the need for treatment, the activity of the administered compound, the general health of the subject, and other considerations well known to the skilled artisan. Generally, they can be administered to a typical human on a daily basis as an oral dose of about 0.1 mg/kg to 1000 mg/kg, and more preferably from about 1 mg/kg to about 200 mg/kg. The parenteral dose will appropriately be 20% to 100% of the oral dose, and i.e., 0.1 mg/kg to 1,000 mg/kg and in embodiments 0.02 mg/kg to 200 mg/kg. While oral administration may be preferable in most instances where the condition is a bone deficit (for reasons of ease, patient acceptability, and the like), alternative methods of administration may be appropriate for selected compounds and selected defects or diseases.

Screening methods may be used to identify in vitro various relatively small molecules that may stimulate endogenous BMP-2 gene expression. Small molecules may be understood as molecules of a size that allow for the molecules to diffuse across cell membranes. The small molecules may exhibit a molecular weight of 1,000 Daltons or less, including all values and ranges between 10 Daltons and 800 Daltons, 800 Daltons or less, 500 Daltons or less, 400 Daltons or less, etc. The small molecules, once identified, may then be applied to various conditions that may benefit from the promotion of tissue healing through the endogenous production of BMP-2, and in particular, bone tissue and/or cartilage healing. In some embodiments, the compound libraries may include those that contain U.S. Food and Drug Administration (FDA) approved drugs, which may be used "off-label" that is for indications other than indications originally approved by the FDA. In addition, drug candidates that have entered phase II clinical trials and other compounds found to treat human diseases, but not FDA approved, may also be screened.

In one embodiment, the screening method may first visually examine induced morphological changes in mesenchymal cells into osteoblast and/or chondroblast morphology using differentiation cues upon the addition of selected compounds. The visually identified compounds stimulating morphological changes into osteoblast and/or chondroblast morphology may then be secondarily screened via polymerase chain reaction (PCR) techniques using mesenchymal cells or pre-osteoblast cells; and then the anabolic effect may be verified using an ex vivo rodent calvaria model. Rodent calvaria model is known by those of ordinary skill in the art to provide a model for human bone and/or cartilage development. Negative controls and positive controls, such as PS-1, Lovastatin, BMP-2 and/or rBMP-2, may be used to verify and compare the morphological changes of the cells during the analysis. The positive controls have been previously identified as directly or indirectly promoting differentiation into osteoblast and/or chondroblast morphology. (J Cell Biochem. 2004 Nov. 15; 93(5):917-28. Fluvastatin and lovastatin but not pravastatin induce neuroglial differentiation in human mesenchymal stem cells. Lee O K, Ko Y C, Kuo T K, Chou S H, Li H J, Chen W M, Chen T H, Su Y.).

As noted above, mesenchymal cells (MSC) may be understood as multipotent cells that may be isolated from bone marrow and differentiate into bone cells (osteoblasts), cartilage cells (chondroblasts) and fat cells (adipocytes). The mesenchymal cells may be sourced from human or animal tissue and may include, for example, human bone marrow derived MSC, cloned mouse embryo derived C3H10T1/2 MSC, or 2T3 mouse pre-osteoblast cells. In one embodiment, mesenchymal cells may be grown in an enhanced cell growth medium and the compounds to be screened may be added to the cells to induce cell differentiation. In another embodiment, the growth medium may be withdrawn and the compositions to be screened may then be added to induce cell differentiation. Compositions that visually appear to promote differentiation into osteoblast or chondrocyte structures may then be selected for further analysis.

Once a number of compounds are initially identified, a secondary screening procedure may be performed wherein up-regulation of BMP-2 mRNA may be observed through polymerase chain reaction (PCR) including real time and/or quantitative PCR. The MSC cells are first treated with selected compounds in solution at various concentrations, such as in the range of 0.1 to 20 μM, including all values therein, such as 1 μM, 5 μM or 10 μM, for a given length of time. After treatment, the PCR specimens may be prepared through various methods known to those of ordinary skill in the art, such as using TAQMAN GENE EXPRESSION CELLS-TO-CT KIT (available from Ambion), or by RNA isolation methods such as acid phenol extractions, glass fiber filter purifications or single-step reagents. PCR may then be performed to determine the up-regulation of BMP-2 gene expression in the MSC cell lines.

The anabolic effect of the compounds down selected through PCR may then be verified. Bone tissue, such as murine calvaria, may be exposed to the compounds identified during secondary screening. The compounds may be provided in solution at various dosages or concentrations in the range of 1 to 20 μM, including all values and increments therein, such as 1 μM, 5 μM or 10 μM. After a time period of exposure, which may be in the range of 10 minutes to 72 hours, or up to 7 days, the tissue may be examined for bone growth.

The compounds identified using the techniques, further described herein, include terfenadine, promethazine, ebastine, carebastine, pheniramine, and astemizole. It is also contemplated that all $H_1$ receptor antagonists, and in particular, first generation and/or second generation $H_1$ receptor antagonists, may exhibit similar stimulation of endogenous BMP-2 up-regulation in a subject, enhancing bone formation and/or cartilage formation. The compounds may be used according to the method of treating bone defects described above. The compounds (terfenadine, promethazine, carebastine, ebastine, pheniramine, and astemizole) may be used alone or in combination such as in combinations of 2, 3, 4, 5, 6, or all of the above compounds. In addition, one or more $H_1$ receptor antagonists may be used, including terfenadine, promethazine, ebastine, carebastine, pheniramine, astemizole and combinations thereof including 2, 3, 4 or all of the $H_1$ receptor antagonists listed above. Particularly, these compounds may be used to stimulate endogenous BMP-2 up-regulation in a subject, which may enhance bone formation and/or cartilage formation. $H_1$ receptor antagonists, including the compounds alone or in combination as listed above, may be provided in the pharmaceutical formulations described supra present in an effective amount to stimulate BMP-2 up-regulation in a subject. In addition, the $H_1$ receptor antagonists, including the compounds alone or in combination as listed above, may be provided in a vessel, such as a vial, a wrapper, etc., in addition to instructions for the administration of the $H_1$ receptor antagonists in an effective amount to stimulate BMP-2 up-regulation in a subject.

EXAMPLES

The following examples and assays are presented for illustrative purposes and are not meant to limit the scope of the disclosure and claimed subject matter attached herein.

Study I:

Visual Observation to Select Candidate Compounds

A cloned mouse embryo derived C3H10T1/2 MSC cell line, which exhibits a relatively stable phenotype and will not spontaneously transform into other cells, once cells have reached confluence, was selected for testing. Conveniently the post-confluent cell line is known to be sensitive to BMP-2 induced chondrogenesis and osteogenenesis (Shea, C. M., et al., "BMP treatment of C3H10T1/2 mesenchymal stem cells induces both chondrogenesis and osteogenesis", J. Cell Biochem, 2003; 90: 1112). The sequence of differentiation follows chondrogenesis→osteogenesis and demands a continuous exposure to BMP-2 or the cells re-differentiate by default into adipocyctes.

The C3H10T1/2 cells were grown in an enhanced growth medium of BGjb (Irvine Scientific, Santa Ana, Calif.). The enhanced medium was withdrawn prior to adding positive controls, BMP-2, Lovastatin and PS-1. Cell differentiation was induced by this protocol and morphological changes were observed by visual observation. It was observed that BMP-2 promoted differentiation into osteoblastic type structure and promoted cell proliferation. Lovastatin and PS-1 generated more elongated looking cells with slowed cell proliferation. While it is possible that some of the osteoblastic type structures identified were chondroblasts, chondroblasts and osteoblasts can appear rather similar since both are symmetric cells and differentiation into either is indicative of the bone repair process.

Once the above visual observation method was verified using the positive controls, a 640 compound library of FDA approved compounds (BIOMOL SCREEN-WELL FDA Approved Drug Library, BML-2841, Enzo chemicals), were screened for morphological differentiation. Specifically, C3H10T1/2 cells were thawed from one frozen cryo-vial and re-seeded into two T-75 tissue culture flasks grown in Alpha MEM with 10% FBS, Glutamine, and Pen/Strip antibiotics. Cells were incubated in a humidified environment at 37° C. and 5% $CO_2$ for 48 hours until the cells reached 80% confluence. After reaching confluence, the C3H10T1/2 cells were trypsinized and re-suspended in pre-warmed growth media to a cell density of $5\times10^4$ cells/mL. Approximately 100 μL of cell suspension was seeded to a 96 well plate to provide 5,000 cells per well. The plate was incubated overnight at 37° C. and spent media was aspirated and replaced with 100 μL of growth media with 5-10 μM of the compounds to be tested. A set of positive (Lovastatin treated) and negative controls (untreated) cells were also prepared.

After 24 hours the cells were observed for morphological differentiation compared to the 10 μM Lovastatin treated cells. Wells that showed morphological differentiation into osteoblasts were designated as positively screened. From the 640 compounds tested, 65 compounds were selected for further study.

Human MSC were similarly studied using a 670 BIOMOL compound library (available from Enzo under product number BML-2841). Specifically, human bone marrow derived mesenchymal cells (hMSC cells) were thawed from one frozen cryo-vial and re-seeded into two T-75 tissue culture flasks grown in Alpha MEM with 10% FBS, Glutamine, and Pen/Strip antibiotics. Cells were incubated in a humidified environment at 37° C. and 5% $CO_2$ for 48 hours until the cells reached 80% confluence. After reaching confluence, the hMSC cells were trypsinized and re-suspended in pre-warmed growth media to a cell density of $5\times10^4$ cells/mL. Approximately 100 μL of cell suspension was seeded to a 96 well plate to provide 5,000 cells per well. The plate was incubated overnight at 37° C. and spent media was aspirated and replaced with 100 μL of growth media with 5-10 μM of the drug compounds to be tested. A set of positive (Lovastatin treated) and negative controls (untreated) cells were also prepared.

After 24 hours, the cells were observed for morphological differentiation compared to the 10 μM Lovastatin treated cells. Wells that showed morphological differentiation into osteoblasts were designated as positively screened. From the 670 compounds 65 compounds were selected for further study.

To further verify the technique, a 2T3 mouse pre-osteoblast cell line derived from calvaria courtesy of Dr. Steve Harris, UTHSCSA, was utilized to visually screen the compounds of the BIOMOL library and JHU libraries, purchased from John Hopkins University including 2387 compounds (solution in wells). Specifically, Murine 2T3 were thawed from one frozen cryovial and re-seeded into two T-75 tissue culture flasks grown in Alpha MEM with 10% FBS, Glutamine, and Pen/

Strip antibiotics. Cells were incubated in a humidified 37° C. under 5% $CO_2$ for 48 hours or when cells reached 80% confluence. After reaching confluency, the 2T3 were trypsinized and resuspended in pre-warm growth media to a cell density of $5\times10^4$ cells/mL. Approximately 100 uL of cell suspension was seeded to a 96 well plate to give a final 5,000 cells per well. Plate was incubated overnight at 37° C. and spent media was aspirated and replace with 100 uL of growth media with 5-10 uM of presumptive drug compounds. A set of controls were untreated and treated with 10 uM of Lovastatin to be used as a visual reference morphological screening. Cells were treated overnight at 37° C. and observed for morphological differentiation compared to the Lovastatin treated cells. Wells that showed morphology changes were designated as positively screened and co-ordinate were recorded for Cell to Ct assay 65 compounds were again primarily selected.

Verification Using PCR

Real Time PCR

To verify BMP-2 up-regulation, secondary molecular biological analysis using real time polymerase chain reaction (PCR) was performed as a secondary screening technique for the compounds identified during visual observation. Specifically, the compounds included those selected through visual observation of the 670 compound library tested using the hMSC cell line as well as those compounds from the BIOMOL and JHU libraries selected through visual observation using the Murine 2T3 line.

Early passage human mesenchymal stem cells (MSC) were thawed from one frozen cryo-vial and seeded into two T-75 tissue culture flasks and incubated at 37° C. for 48 hours in Alpha MEM with 10% FBS. After three days and one refeeding, the cells were trypsinized and re-suspended in pre-warmed media at $5\times10^4$ cells/mL to provide 5,000 cells per well in a 96 well plate and incubated overnight at 37° C. in 5% $CO_2$. Spent media was aspirated from each well and replaced with 5-10 μM drug solution (positively screened by image analysis) in 100 μL growth media.

After 24 hours, the wells were prepped using TAQMAN GENE EXPRESSION CELLS TO CT KIT from Ambion, Inc., following the recommended instructions (Ambion #4399002). Each well was washed in cold PBS, lysed at room temperature for five minutes, and stop reagent added to each well to stop the lysis reaction. The final lysate was kept cold at 4° C. and used immediately as the RNA template for the reverse transcription cDNA synthesis following the TAQMAN GENE EXPRESSION CELLS TO CT KIT instructions.

The cDNA synthesis was prepared on a separate sterile 96-well PCR plate and performed on the Step One Plus Real Time PCR System instrument (Applied Biosystems) with the programming set at 37° C. for 60 minutes and an inactivation hold of 95° C. for five minutes. The final cDNA reaction was kept cold and used as the template for the TAQMAN GENE Real-Time PCR step following the recommended instructions for TAQMAN GENE EXPRESSION CELLS TO CT KIT assay. For the TAQMAN gene expression, gene-specific fluorescent labeled TAQMAN primers for FAM-BMP2 (Applied Biosystems, Hs00154192.m1), FAM-BMP2 (Hs00370078_m1), and TaqMan reference VIC-18S ribosomal RNA (Applied Biosystems, 4310893E) were used to target genes of interest. A cocktail of universal master mix (Applied Biosystems, 4369016) was prepared individually for the sets of primers which contained Taq Polymerase, dNTPs, and buffer. Template cDNA's were added separately to respective individual wells in replicate samples.

The PCR was performed on the STEPONEPLUS Real-Time System instrument (Applied Biosystems). The amplification program consisted of 1 cycle of 95° C. with 10 minute hold (hot start) and followed by 50 cycles of 95° C. with 15-second annealing hold and 1-minute 60° C. specified acquisition hold. Upon completion of the program, the data was evaluated by comparing the changes in BMP-2 gene expression (mRNA level) induced by the compounds. Of the 65 compounds initially identified exhibiting morphological changes, 35 were found to exhibit 3 fold or more, positively indicating BMP-2 up-regulation.

Drug compounds that showed significant fold change compared to an untreated control were further analyzed for signaling pathway activities using the Lentiviral Cell Signaling Pathway Luciferase Reporter assay (SABiosciences # CCA-001L). However, clear results were not obtained.

Further Quantitative PCR

Human mesenchymal stem cells (LONZA, Catalog PT2501) were maintained in Mesenchymal stem cells basal media (MSCBM CAT#PT-3238). Early passage cells were plated in triplicate at $2\times10^4$ cells/cm$^2$ using six well tissue culture plates and grown in humidified 5% $CO_2$ at 37° C. for 24 hours. Spent media was replaced by assay media of drugs to be tested in same media as above at 10 μM final concentration. Untreated cells were used as the control group. Total RNA were prepared using either TRI Reagent (Ambion, Cat. 9738), for subsequent TaqMan gene expression qPCR of BMP2. RNA concentration and integrity was assessed by absorbance 260/280 and electrophoresis in 1% Agarose with formaldehyde loading dye. For TaqMan gene expression, cDNA was synthesized from 2 μg of total RNA using the High Capacity cDNA Reverse Transcription Kit (Applied Biosystems, Cat. 4368814). The resulting cDNA were diluted 1:100 for TaqMan and amplified by real-time quantitative PCR. Gene-specific fluorescent labeled TaqMan primers for FAM-BMP2 (Applied Biosystems, Hs00154192.m1) and TaqMan reference VIC-18S ribosomal RNA (Applied Biosystems, 4310893E) were used to target gene of interest. A cocktail of universal master mix (Applied Biosystems, 4369016) were prepared individually for both set of primers which contained Taq Polymerase, dNTPs, and buffer. Template cDNA's were added separately to respective individual wells in triplicate samples. The PCR were performed on StepOne Plus Real Time System instrument (Applied Biosystems). The amplification program consisted of 1 cycle of 95° C. with 10 minute hold (hot start) followed by 50 cycles of 95° C. with 15 second annealing hold and 1 minute 60° C. specified acquisition hold. The Ct value of endogenous reference gene (i.e. 18 s) was used to control for input RNA and then used to normalize target gene (i.e. BMP2) tested from the same cDNA sample to calculate the Δ Ct, and then calibrated to an internal reference sample. Change in gene expression was determined by the expression ΔΔCt relative method.

Of the 32 compounds verified as being positive or negative for BMP-2 upregulation using real-time PCT, 23 Compounds were found to positively up-regulate BMP-2 using qPCR. Up-regulation of BMP-2 mRNA by selected drugs can be observed by either method. 18 compounds were confirmed positive by the more stringent qPCR techniques. Twelve (12) positive controls (Table 1), known to up-regulate BMP-2 gene expression, included as blind controls were confirmed positive, thus adding additional validation to the results. Table 2 includes a list of BMP-2 positive compounds confirmed by qPCR after screening the BIOMOL library and Table 3 includes of BMP-2 positive compounds confirmed by qPCR after screening the John Hopkins University Library. Included in the tables is the target or common medical use for each compounds. It is also noted that a person having ordinary skill in the art may recognize that samples exhibiting fold increases over 1,000 are indicative of improper measurement procedure and the data generated in such samples may be unreliable.

TABLE 1

List of BMP-2 Positive Control Compounds Confirmed by qPCR and RT-PCR

| RT PCR Fold increase | q-PCR Fold increase | Drug | Target | mechanism |
|---|---|---|---|---|
| 5.3 | 11.9 | Cerivastatin | Cholesterol | HMG-CoA |
| 59.9 | 10.7 | Lovastatin | Cholesterol | HMG-CoA |
| 3.2 | 7.8 | Fluvastatin Na | Cholesterol | HMG-CoA |
| 3.1 | 0.9 | Mevastatin | Cholesterol | HMG-CoA |
| 4.2 | 2.3 | Simvastatin | Cholesterol | HMG-CoA |
| 23.5 | 1.5 | Shikonin | Cancer | Proteasome inhibitor |
| 15.4 | 2.4 | Bortezomib | Cancer | Proteasome inhibitor |
| 3.7 | 4.0 | Taxol | Cancer | Micro tubule Inhibitor |
| 11.0 | 2.7 | Docetaxil | Cancer | Micro tubule Inhibitor |
| 12.4 | 1.8 | Vindesine | Cancer | Micro tubule Inhibitor |
| 10.8 | 1.8 | Vincristine sulfate | Cancer | Micro tubule Inhibitor |
| 9.5 | 1.7 | Vinblastine sulfate | Cancer | Micro tubule Inhibitor |

TABLE 2

BMP-2 Active Compounds Found after qPCR screening BIOMOL library (670 compounds screened)

| RT PCR Fold increase | q-PCR Fold increase | Name | Common medical use | Intracellular molecular target |
|---|---|---|---|---|
| 52.9 | 95.0 | Quinacrine | Malaria | PLA2 Inh H1 antagonist |
| 122.3 | 54.6 | Puromycin | Cancer | Translation Inh |
| 309.8 | 17.6 | Auranofin | Arthritis | Bone active |
| 32.6 | 14.2 | Lomofungin | Parasites | Anthelmintic |
| 13.9 | 10.4 | Terfenadine | Allergies | H1 receptor antagonist |
| 4.6 | 7.3 | Apomorphine r (−) | Depression | Bone active |
| 4.9 | 6.6 | Miglustat | Gaucher disease | Bone active |
| 8.2 | 6.2 | Debrisoquin sulfate | Drug metabolism studies | Metabolism |
| 6.8 | 4.0 | Prazosin | Hypertension | Alpha blocker |
| 29.0 | 4.0 | Camptothecin | Cancer | Topo I inh |
| 30.0 | 3.9 | 10-hydroxy-camptothecin | Cancer | Topo I inh |
| 6.0 | 3.4 | Calcifediol | Metabolic Bone Disease | Vit D Pro hormone |
| 3.6 | 2.4 | Maprotiline | Depression | H1 rec atag |
| 6.6 | 2.0 | Fenbendazole | Parasites | Anthelmintic |
| 5.6 | 1.7 | Flubendazole | Parasites | Anthelmintic |
| 9.7 | 1.6 | Flutamide | Cancer | Antiandrogen |
| 4.5 | 1.4 | Oxibendazole | Parasites | Anthelmintic |
| 156.2 | 1.0 | Astemizole | Malaria | H1 recep antag |

TABLE 3

BMP-2 active compounds found in JHU library (2,387 compounds screened)

| Compound tested | Fold change (BMP-2) |
|---|---|
| Aminacrine (9-Aminoacridine) | 5762.00 |
| Acriflavine hydrochloride | 1491.00 |
| Vinorelbine tartrate | 803.00 |
| Quinacrine | 722.00 |
| Anisomycin | 670.00 |
| Pyrvinium pamoate | 398.00 |
| Topotecan | 365.00 |
| Anisomycin | 387.00 |
| Emetine | 220.00 |
| Lovastatin (Mevinolin) | 182.00 |
| Proflavine hemisulfate salt hydrate, powder | 177.00 |
| Brilliant Blue | 111.00 |
| Amsacrine | 85.00 |
| Desmethyl astemizole | 75.00 |
| Ipecac syrup | 75.00 |
| Vinblastine sulfate | 64.00 |
| ROTENONE | 61.00 |
| Vincristine sulfate | 57.00 |
| Triciribine | 42.00 |
| THIRAM | 36.00 |
| 6alpha-METHYLPREDNISOLONE ACETATE | 35.00 |
| SIMVASTATIN | 34.00 |
| Cycloheximide | 34.00 |
| Podophyllum resin | 31.00 |
| Lomofungin | 26.00 |
| Saponin, from quillaja bark | 26.00 |
| THIMEROSAL | 23.00 |
| Nitroxoline (8-hydroxy 5-nitroquinoline) | 18.00 |
| Oxibendazole | 18.00 |
| Phytic acid, dodecasodium salt hydrate | 15.00 |
| Clofoctol | 11.00 |
| Flubendazole | 10.00 |
| Diosmin | 9.00 |
| Phenylbutyrate Sodium | 8.00 |
| Cadmium Acetate | 8.00 |
| Verteporfin | 6.00 |
| Thiostrepton | 5.00 |
| Laslocid Sodium | 4.00 |
| 10 µM Lova | 18.00 |
| 10 µM PS1 | 33.00 |
| 24-6 h | 20.00 |
| 24-8 h | 15.00 |
| Non-treated | 1.00 |

Anabolic Assays Using Mouse Calvaria

To investigate the biological effects on bone of the downselected compounds from the PCR assays a number of assays were performed using murine calvaria bone as follows. Murine calvaria bone was removed from new born mice (Harlan Sprague Dawley). Specifically, 4-day-old pups were dipped into 95% ETOH and the head was cut off relatively quickly using regular small scissors followed by removal of the skin from the calvaria using forceps and scissors. The collected tissue was dipped into BGJb Medium (Invitrogen Cat#12591)+L-Glutaime with 1% Pen/Strep and 1% bovine serum albumin, in order to keep the calvaria bone from drying.

The calvaria bones were then cut using curved scissors to make a cut along the suture of the calvaria bone and carefully remove the two parts of calvaria, illustrated in FIG. 1 items 10, 12, from the brain and trim the calvaria avoiding the suture area. Calvaria from each carrier were then pooled in the same Petri dish. The dish was placed into a 37° C. and 5% $CO_2$ incubator after all the pups from the same carrier were processed.

The down selected compounds were prepared in a solution of dimethyl sulfoxide (DMSO) to form stock solutions. Specifically, 100 mM and 50 mM stock solutions were prepared for each compound. The concentrations of the solutions were then adjusted by adding the stock compound to BGJ media with 0.1% bovine serum albumin, which was prepared for each treatment group in a 10 ml centrifuge tube. To obtain 1 μM concentration treatment solution, 1 ml of the stock solution was combined with 4 ml of the media. To obtain 5 μM concentration treatment solution, 2.5 ml of stock was added to 2.5 ml of the media. To obtain 10 μM concentration treatment solution 12 μl of 5 mM stock was added to 6 ml of media.

Figure 2:
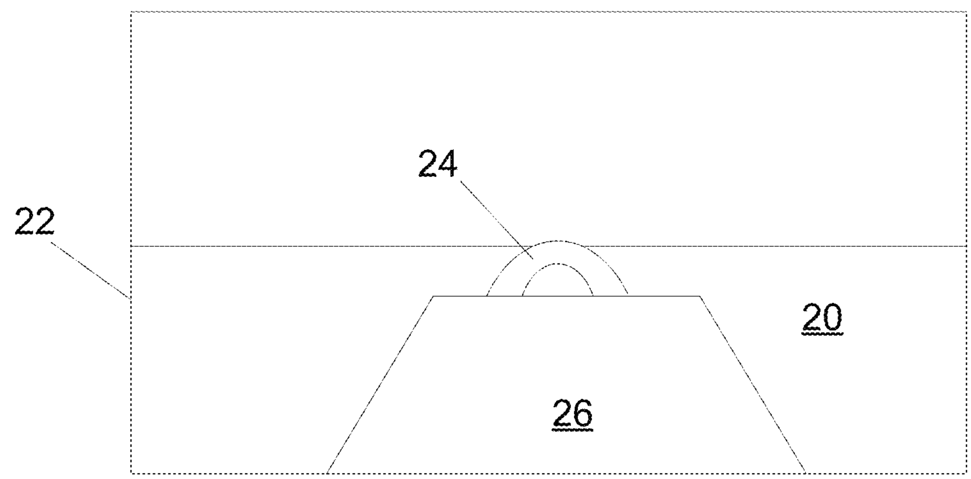
FIG. 2 illustrates a schematic of an exemplary test set-up for the murine calvaria assays.
Figure 3:
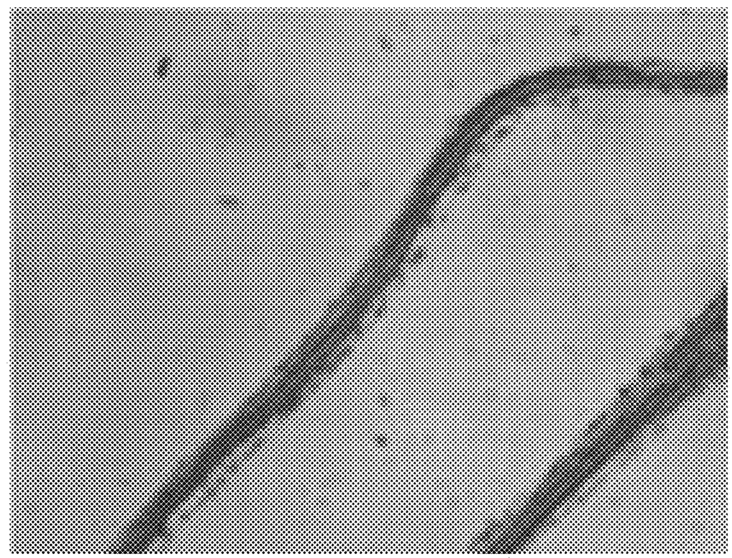
FIGS. 3 through 54 illustrate histological images of the murine calvaria samples after treatment.
Figure 4:
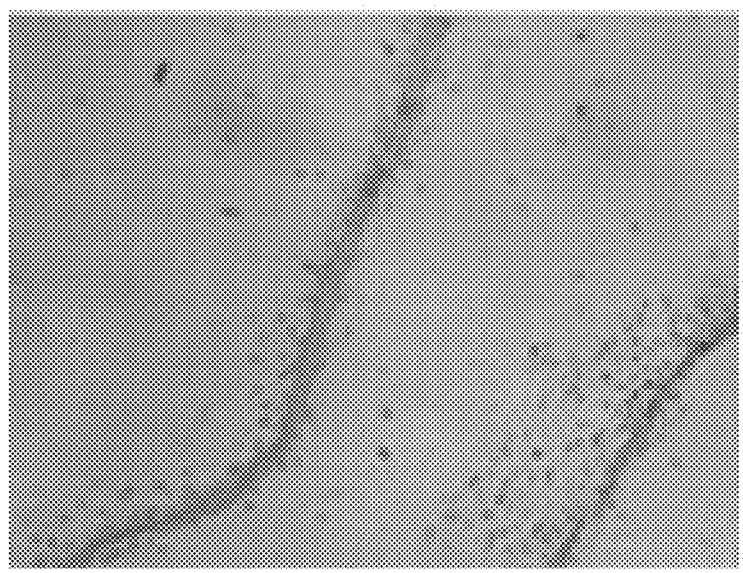
Figure 5:
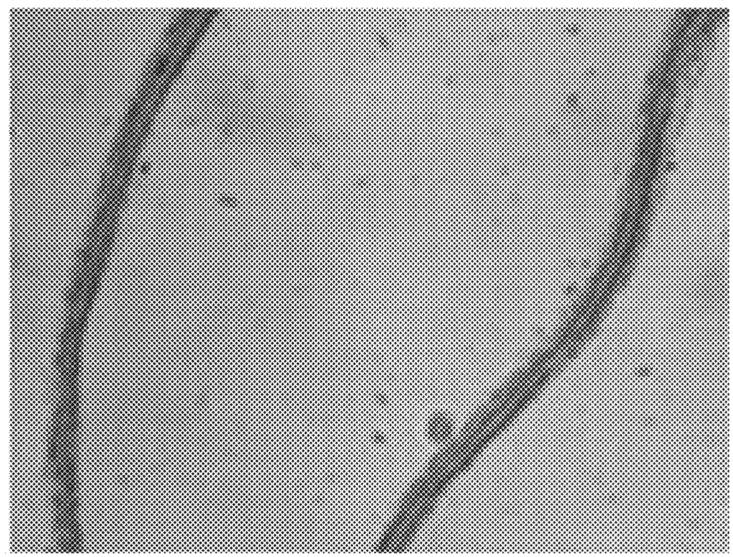
Figure 6:
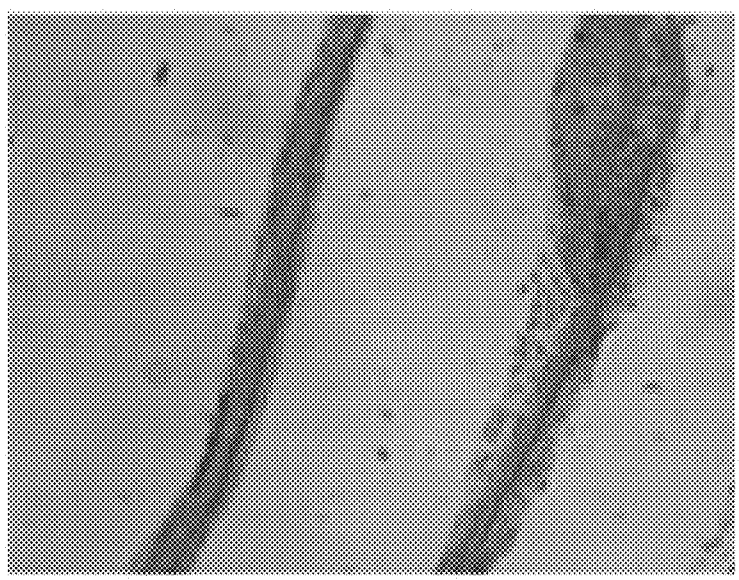
Figure 7:
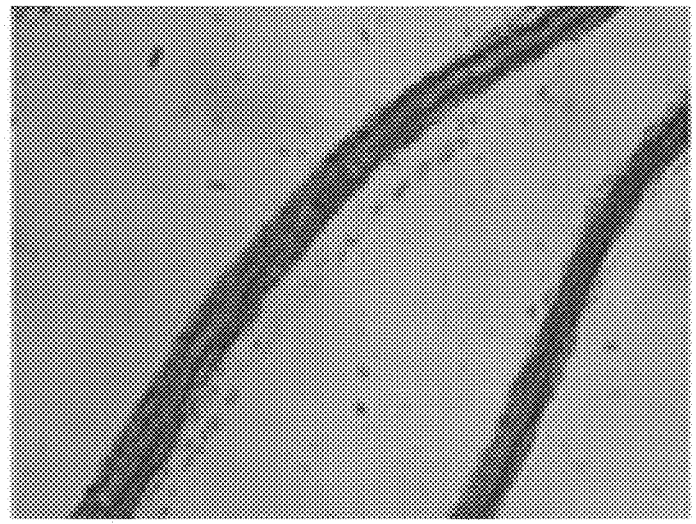
Figure 8:
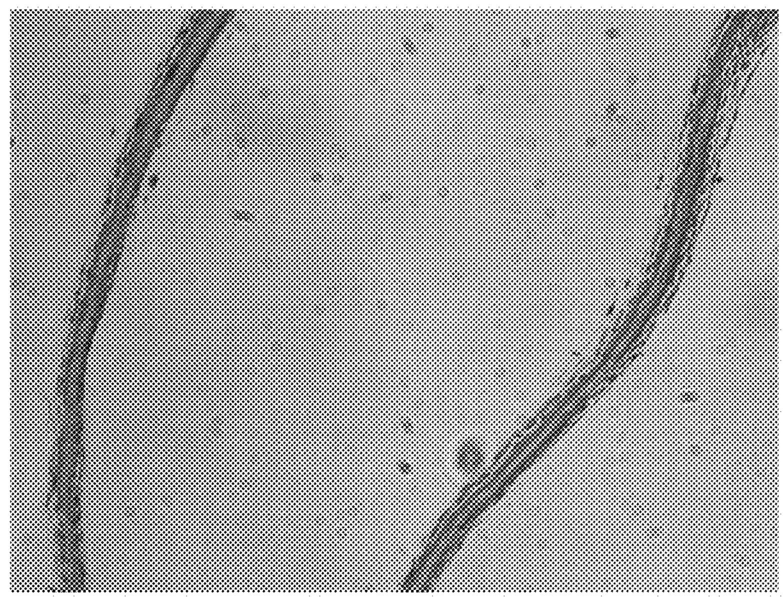
Figure 9:
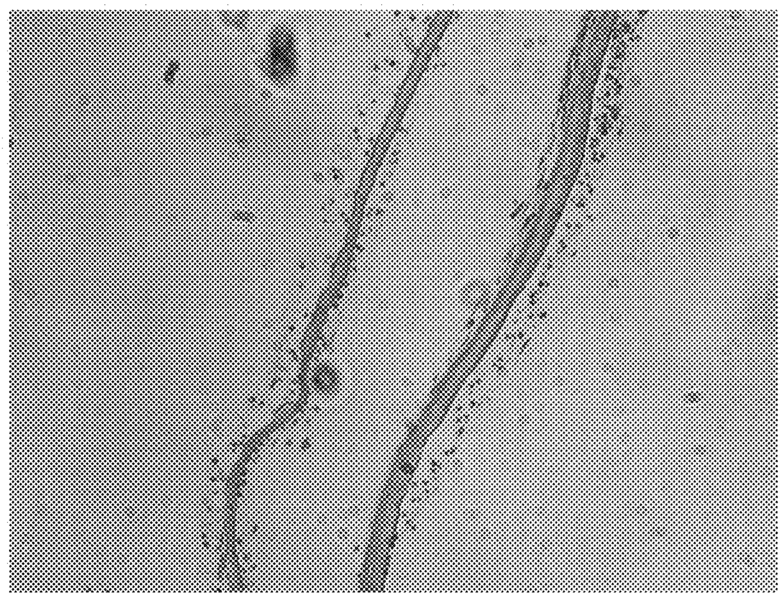
Figure 10:
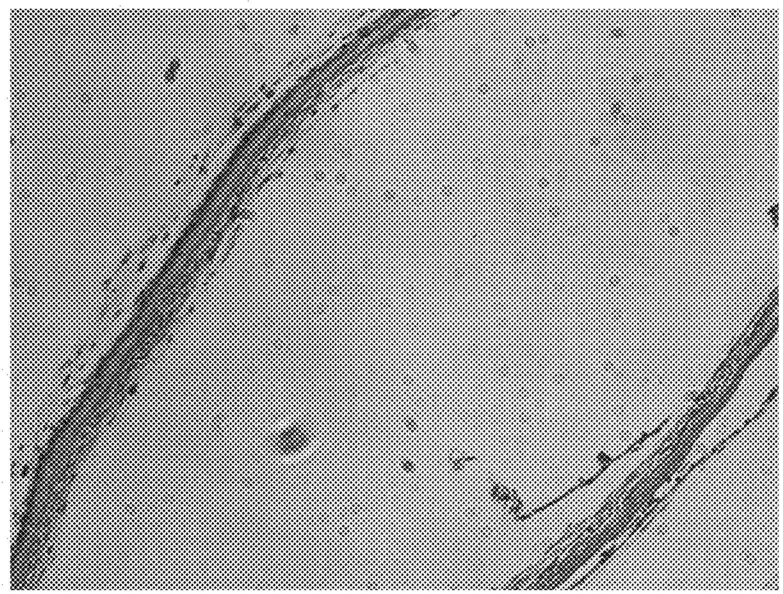
Figure 11:
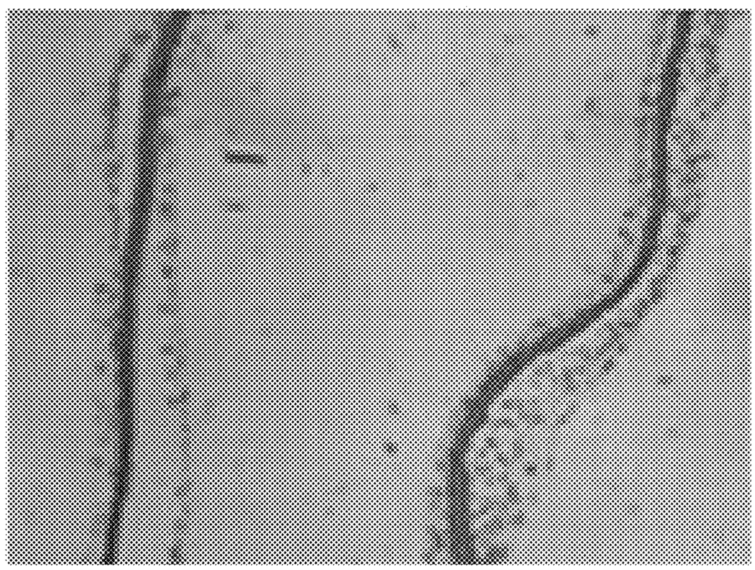
Figure 12:
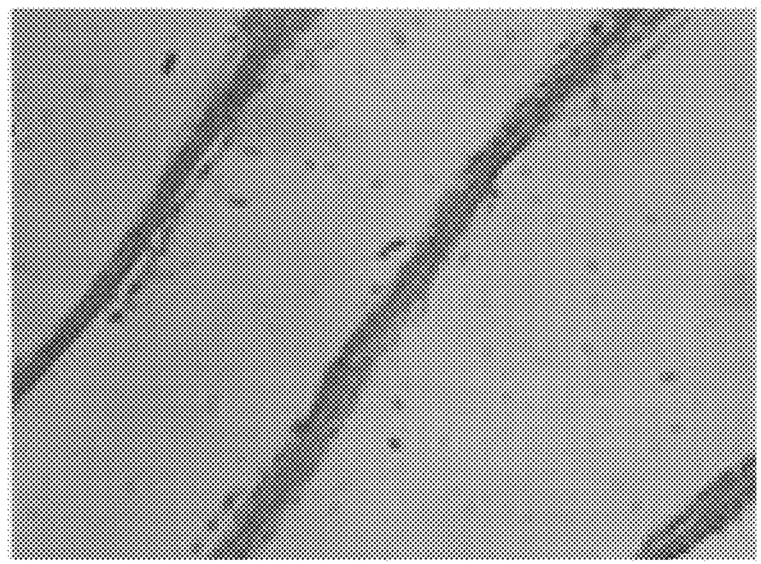
Figure 13:
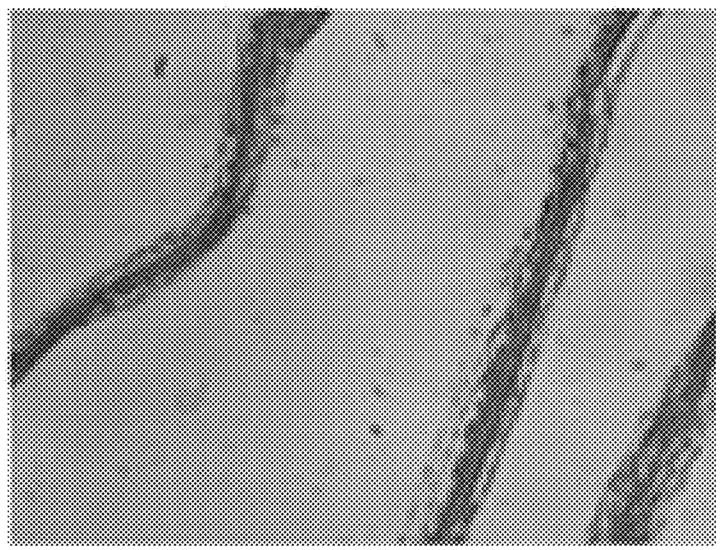
Figure 14:
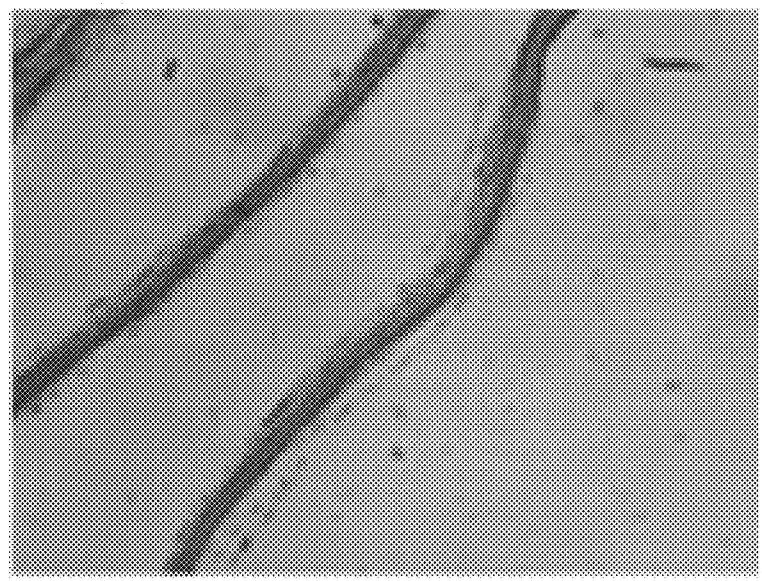
Figure 15:
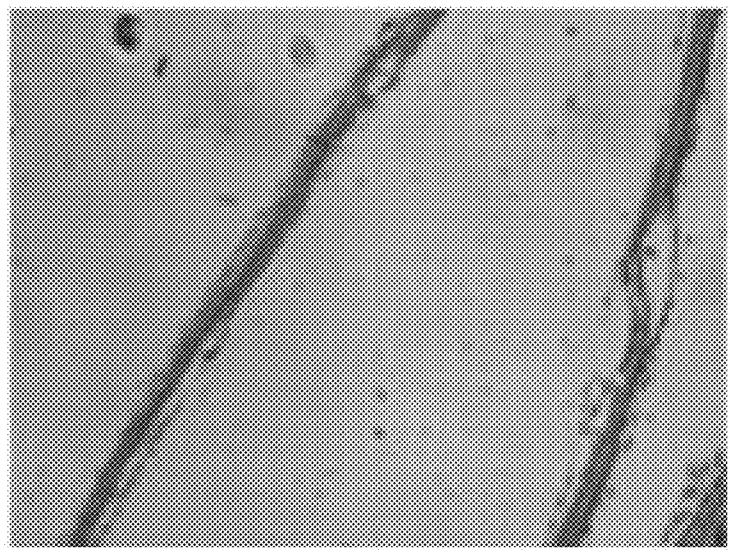
Figure 16:
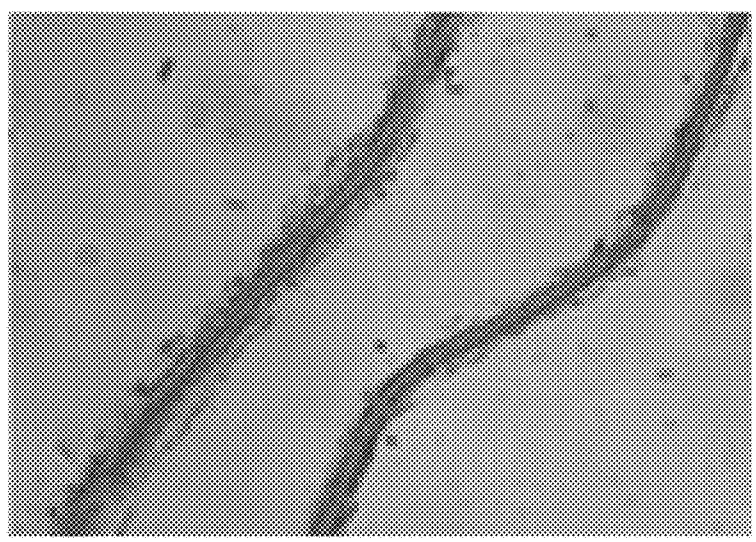
Figure 17:
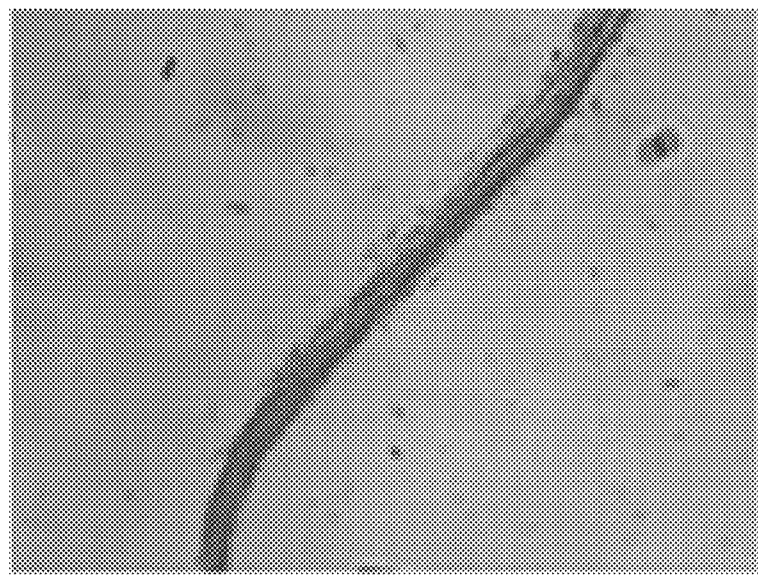
Figure 18:
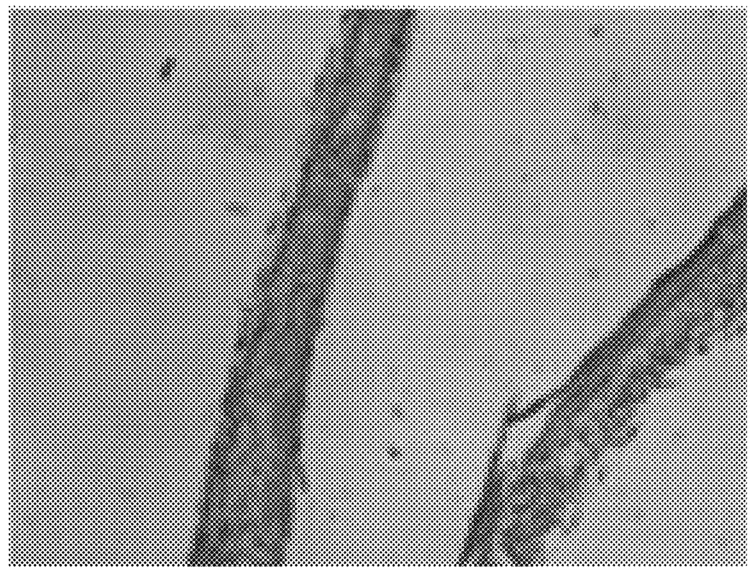
Figure 19:
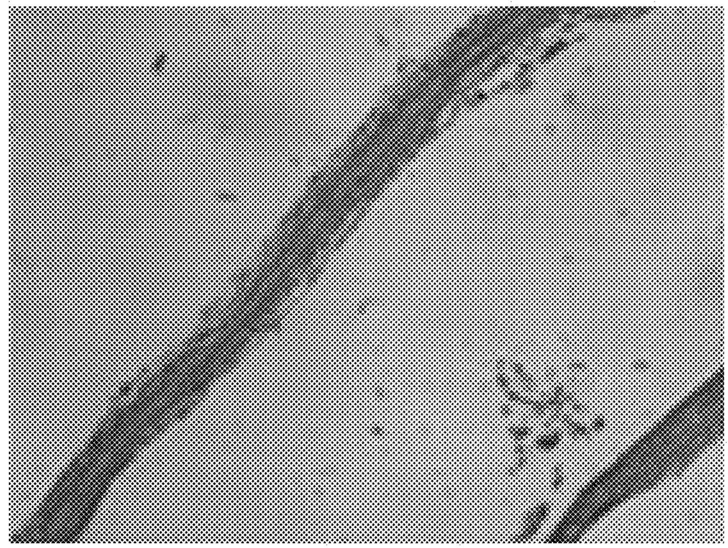
Figure 20:
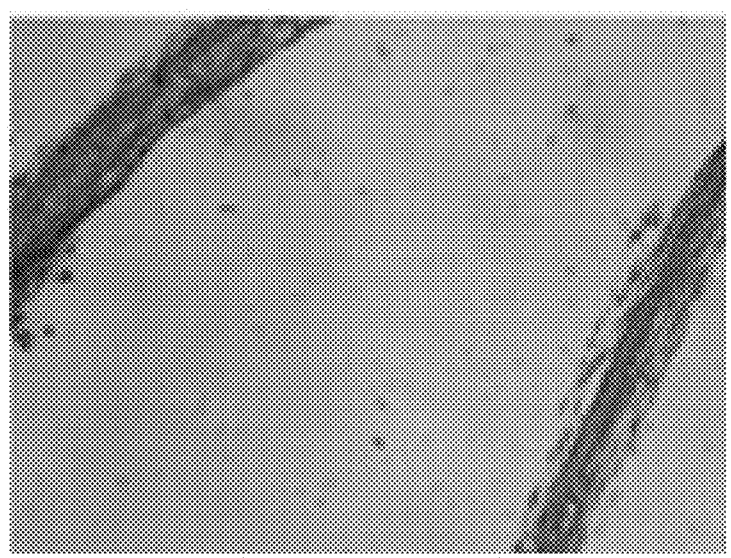
Figure 21:
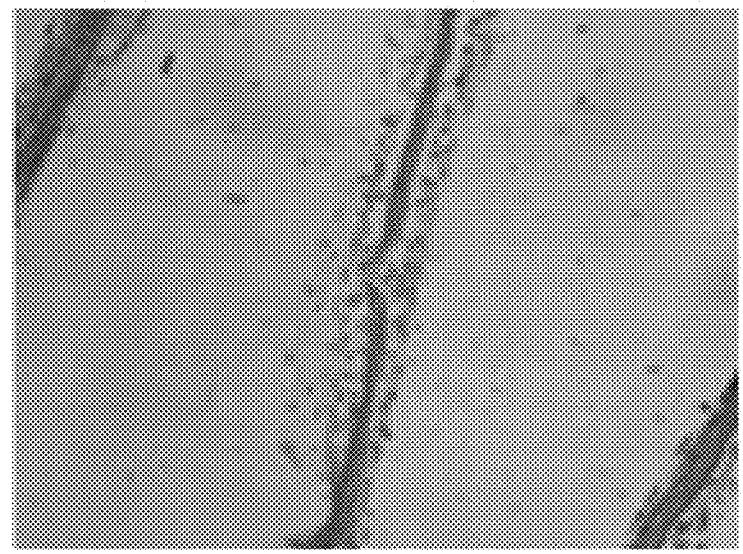
Figure 22:
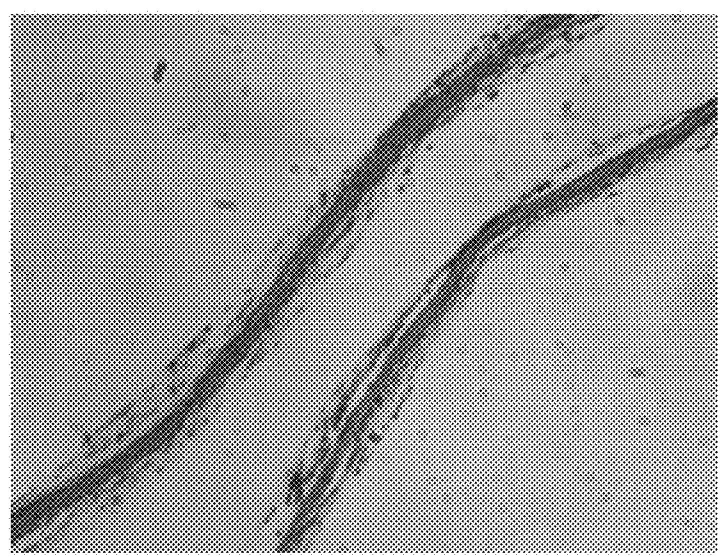
Figure 23:
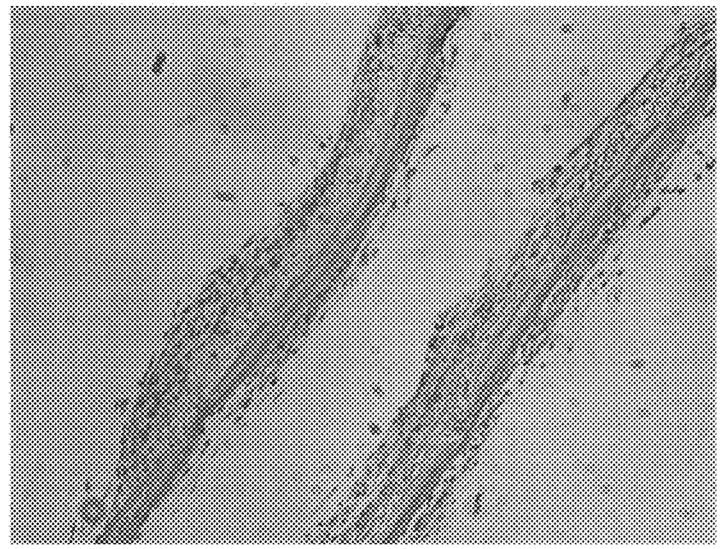
Figure 24:
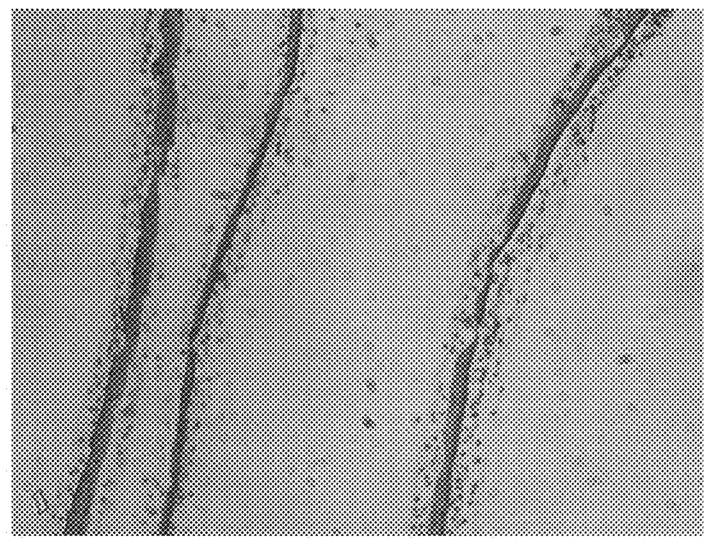
Figure 25:
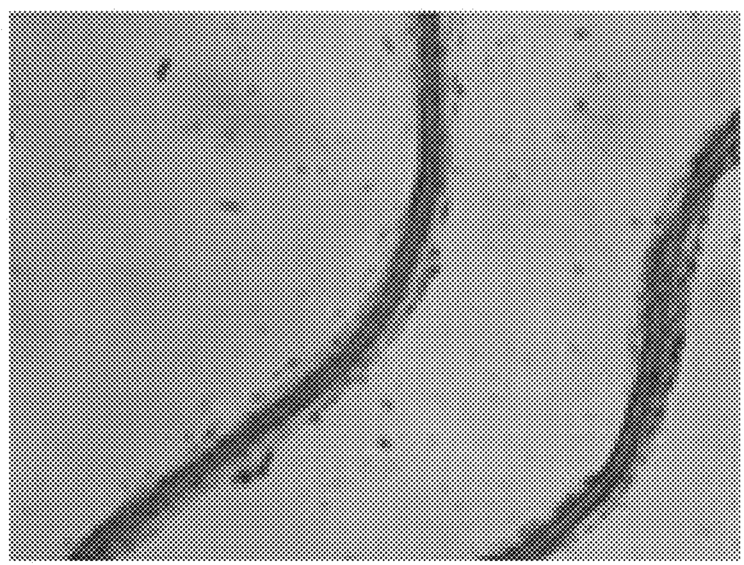
Figure 26:
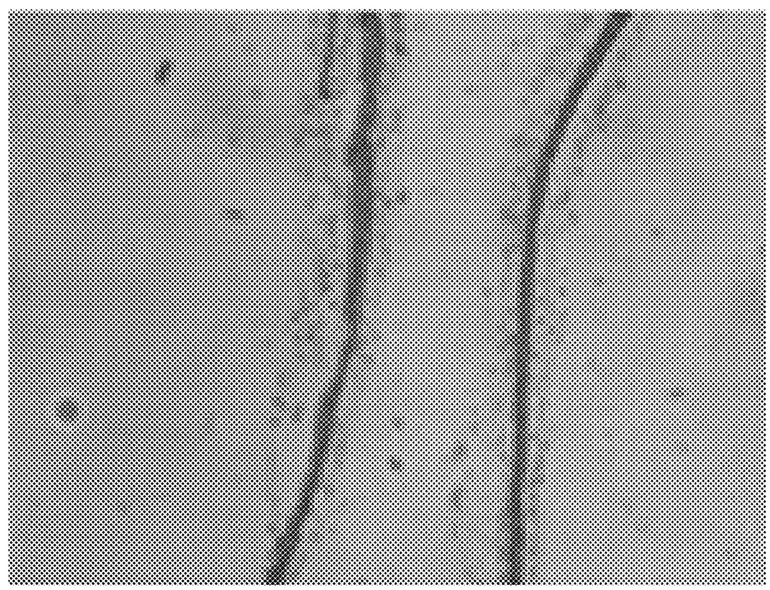
Figure 27:
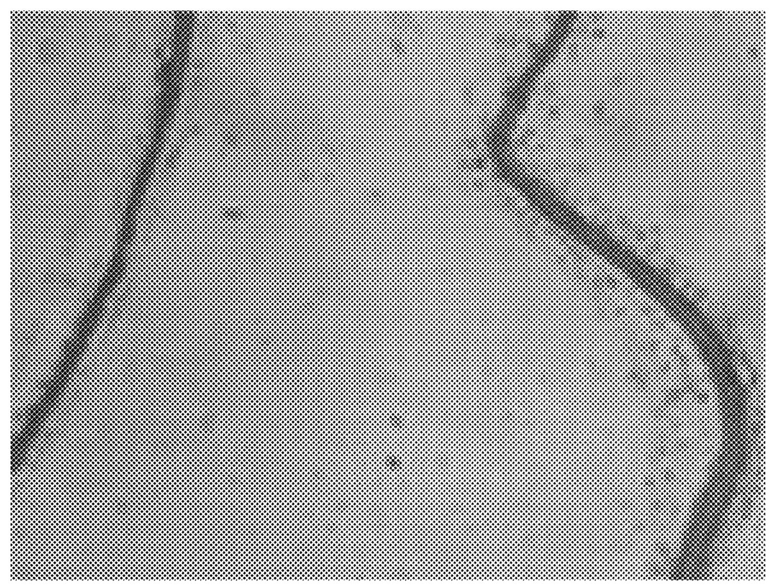
Figure 28:
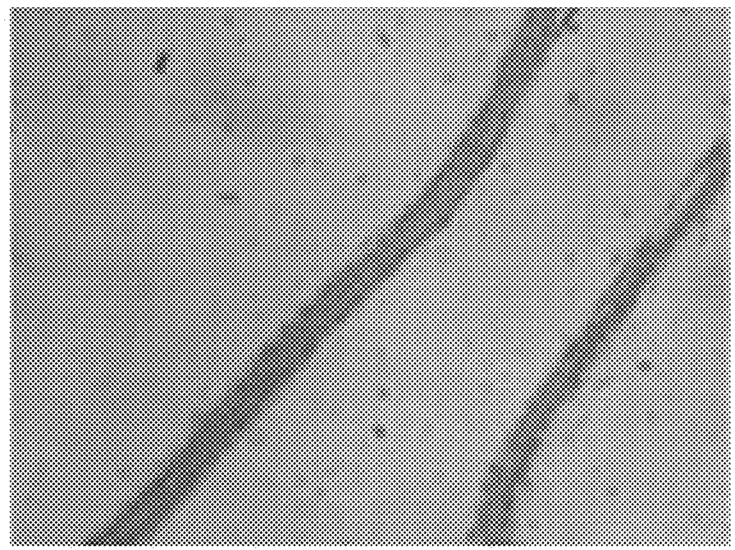
Figure 29:
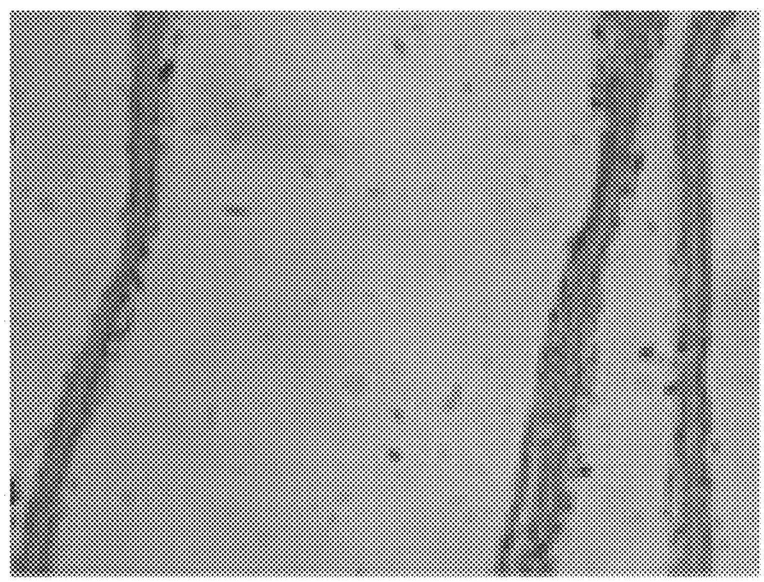
Figure 30:
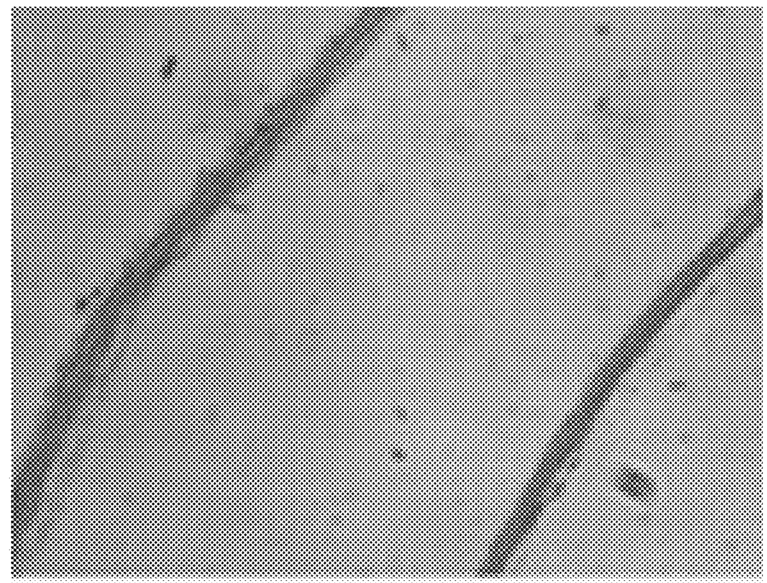
Figure 31:
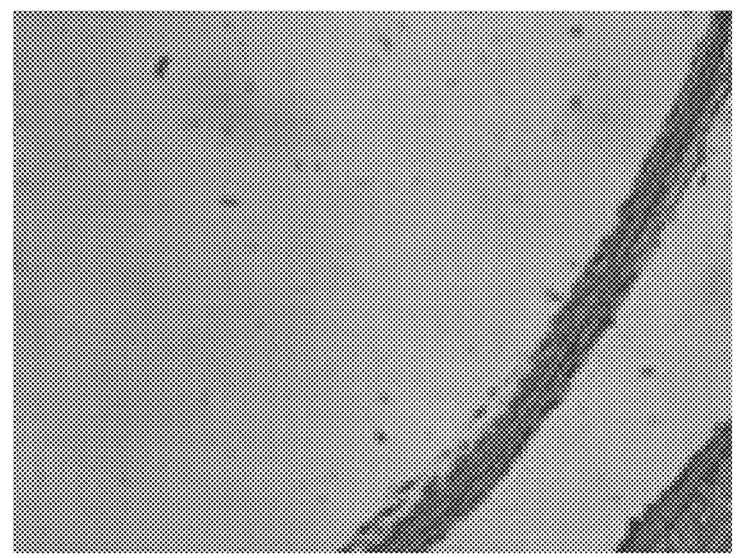
Figure 32:
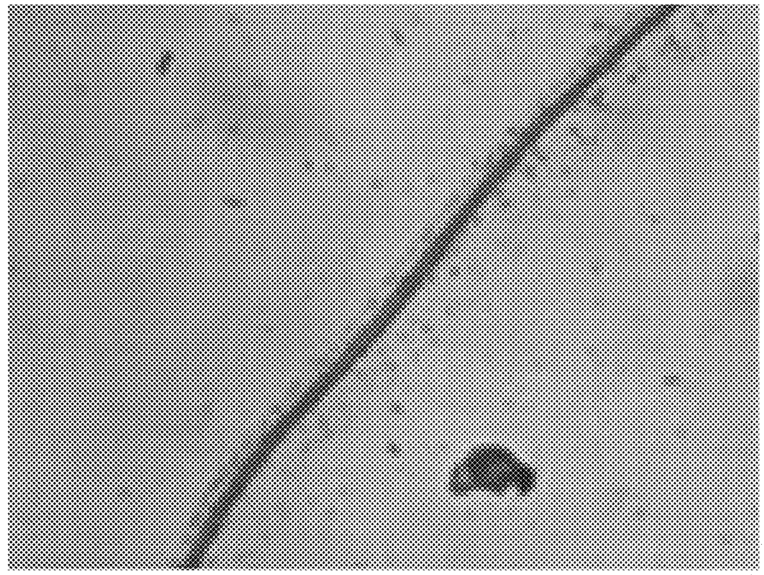
Figure 33:
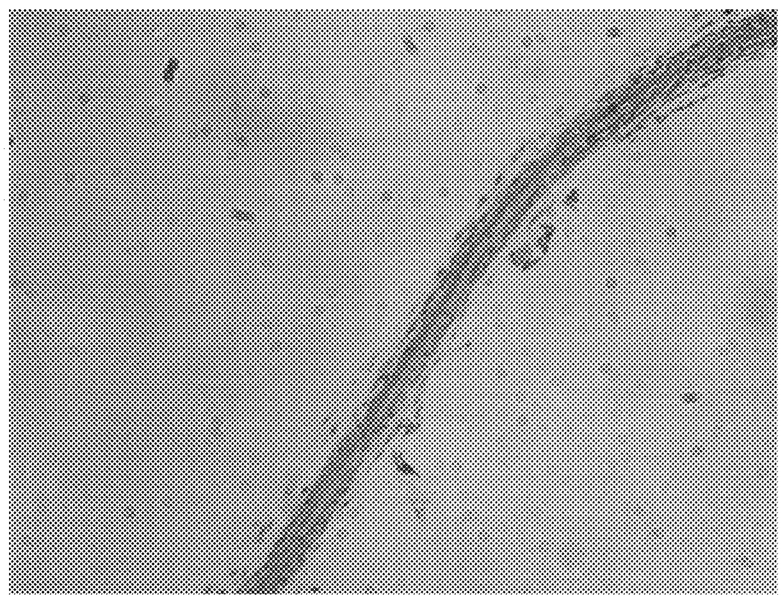
Figure 34:
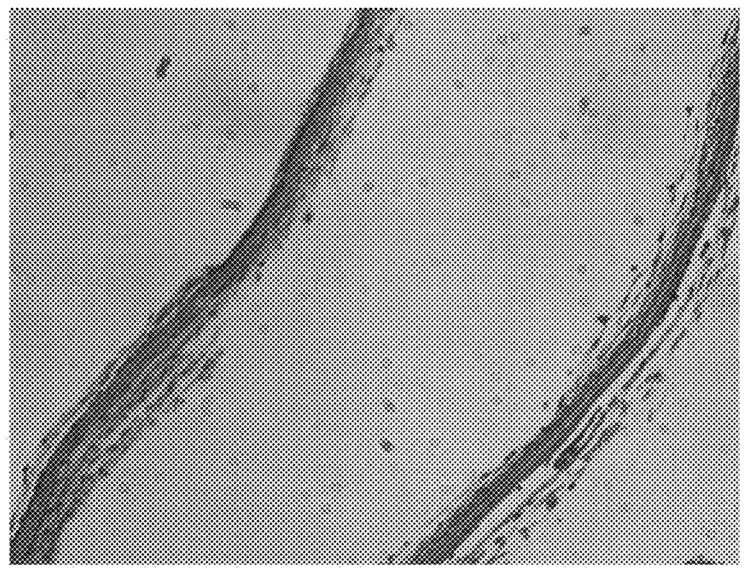
Figure 35:
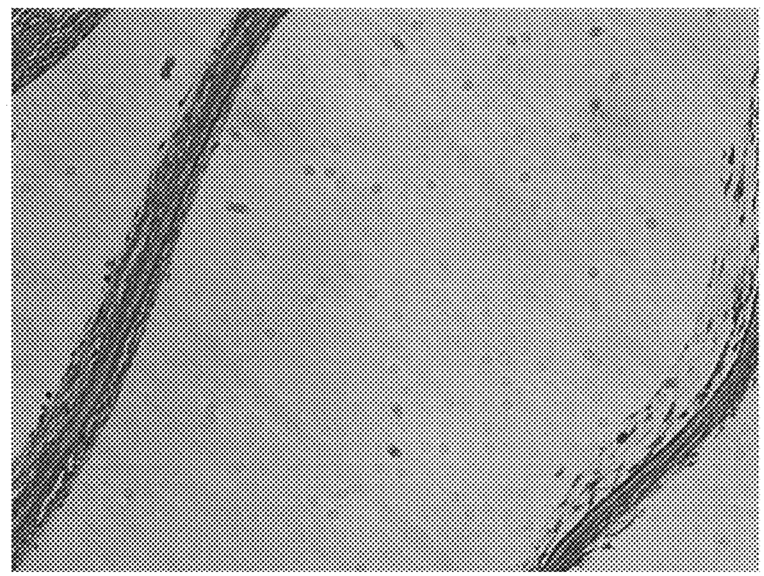
Figure 36:
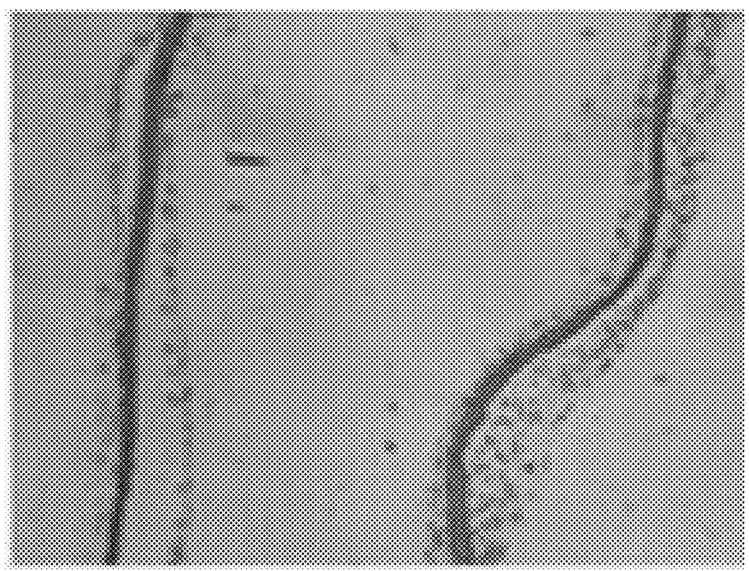
Figure 37:
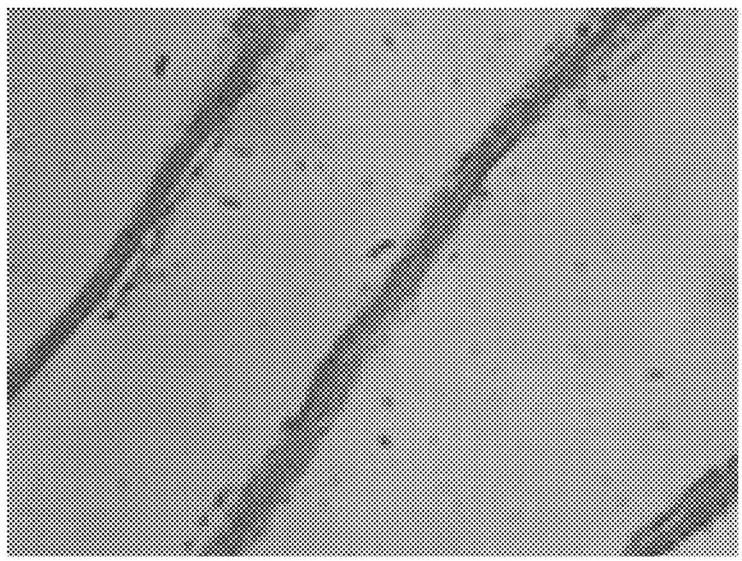
Figure 38:
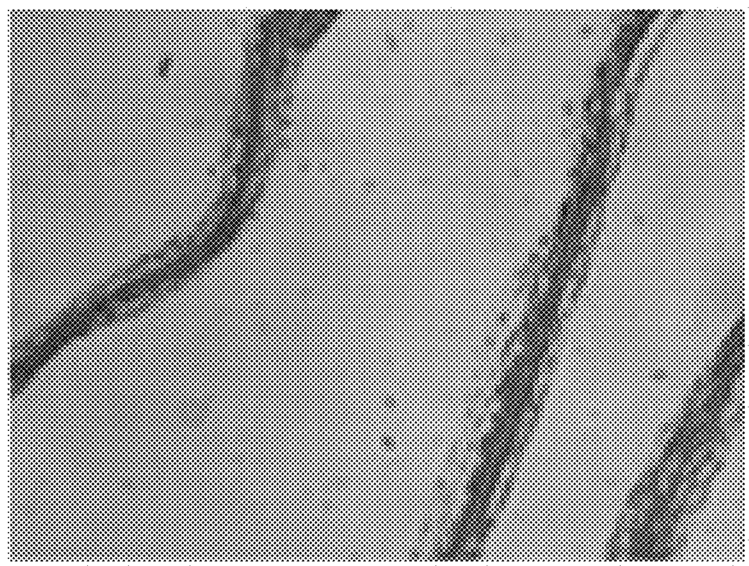
Figure 39:
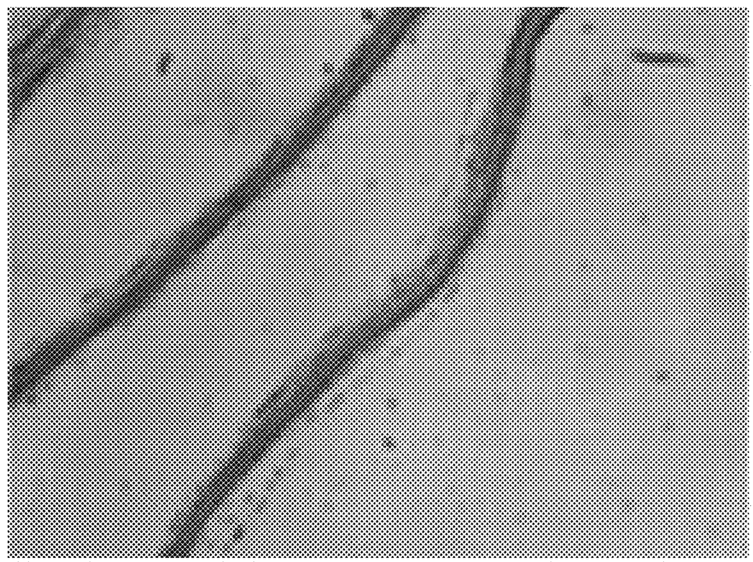
Figure 40:
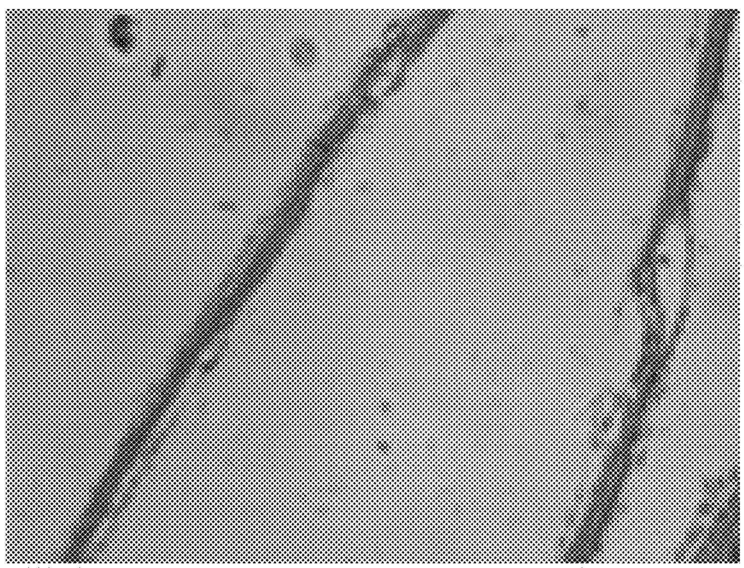
Figures 41, 42:
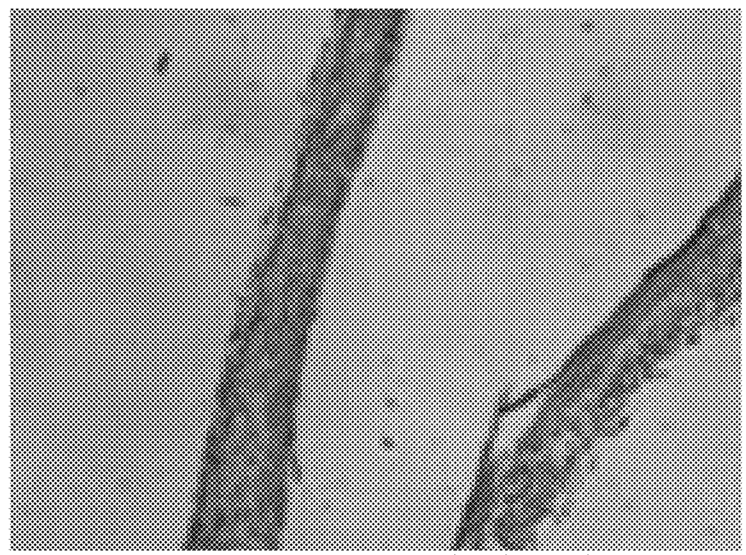
Figure 43:
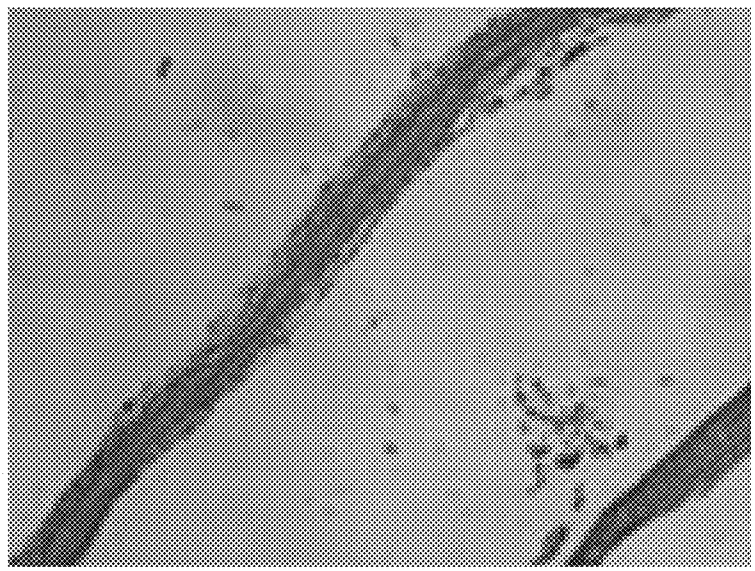
Figure 44:
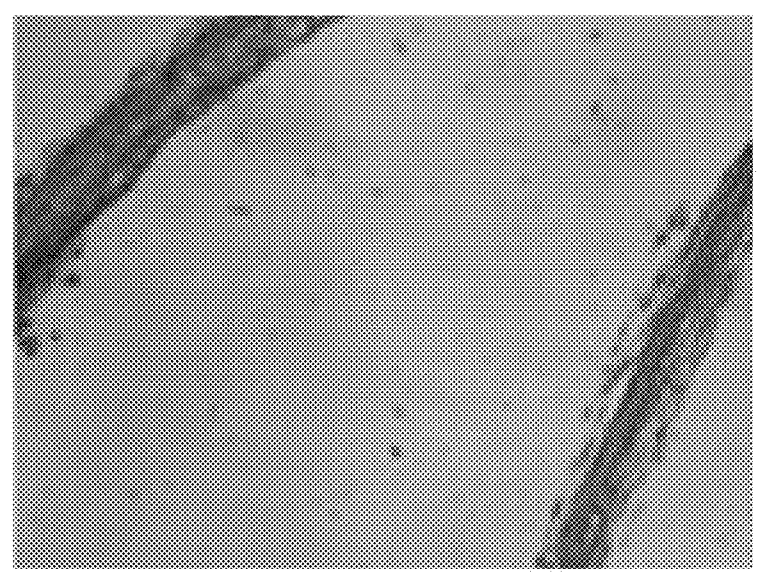
Figure 45:
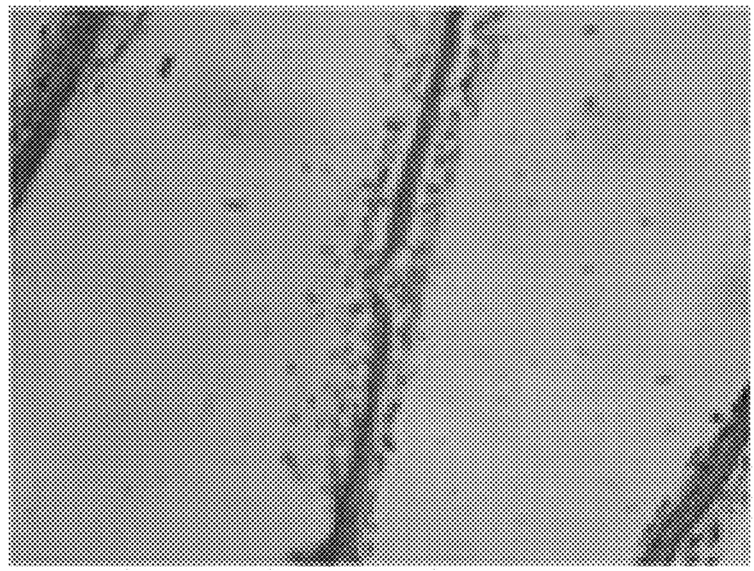
Figure 46:
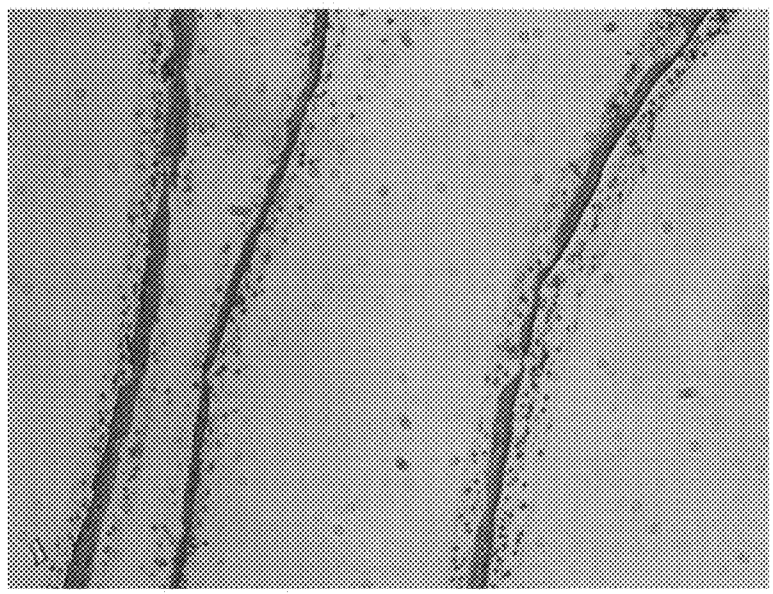
Figure 47:
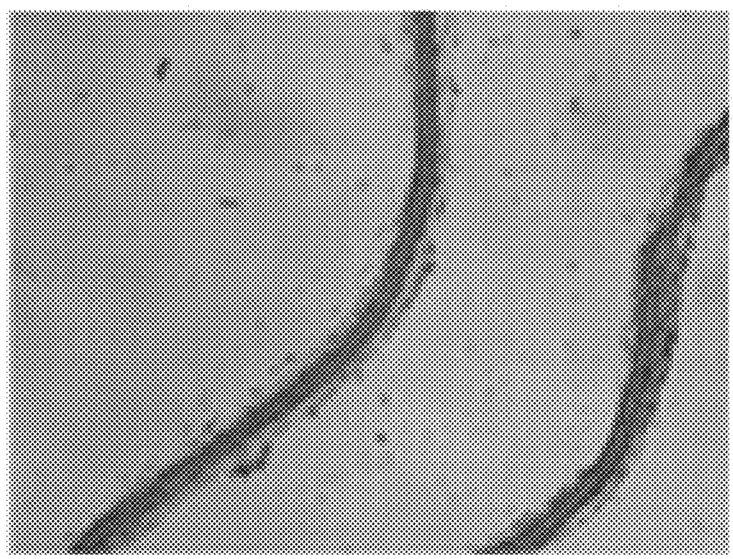
Figure 48:
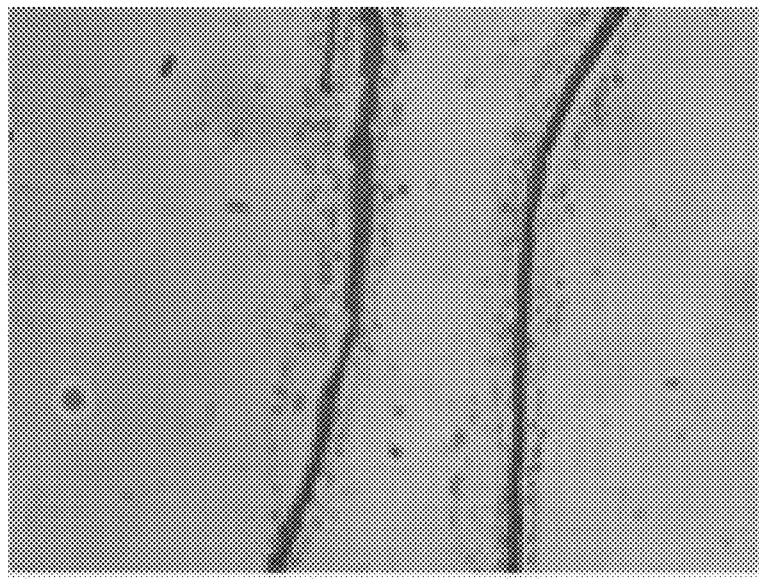
Figure 49:
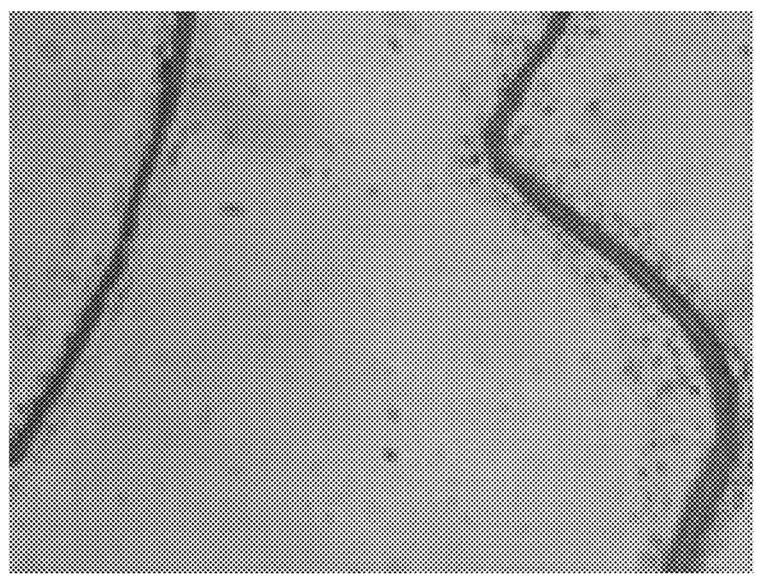
Figure 50:
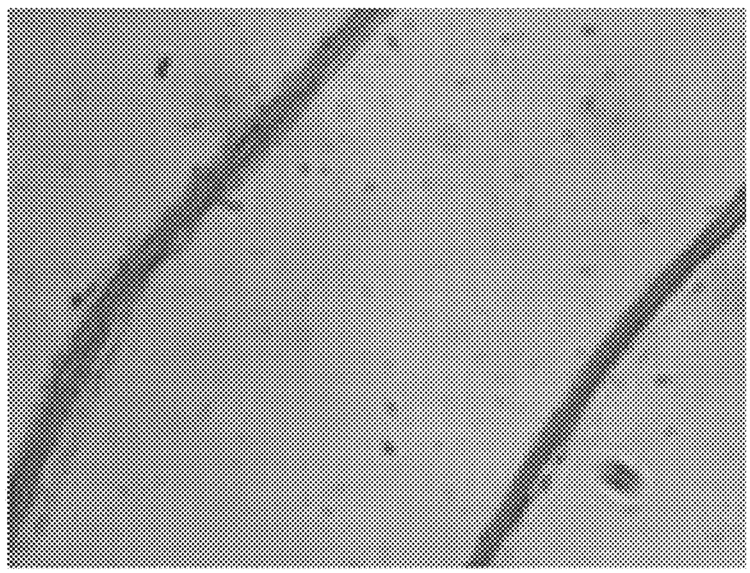
Figure 51:
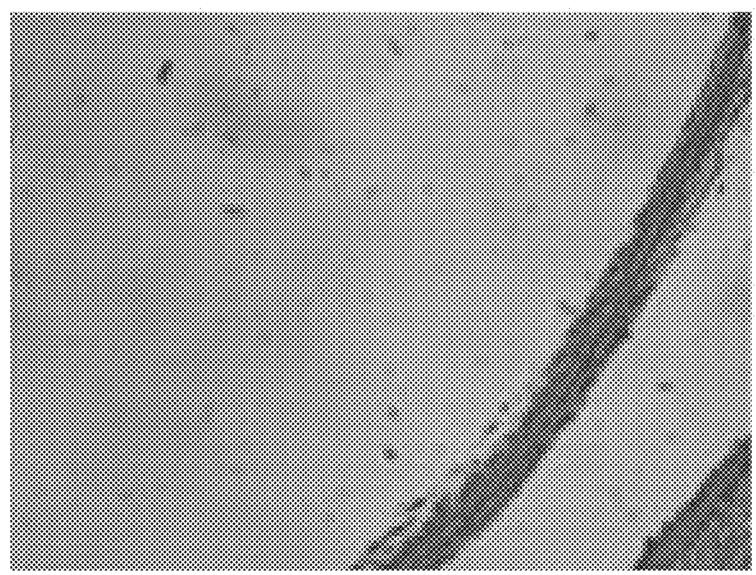
Figure 52:
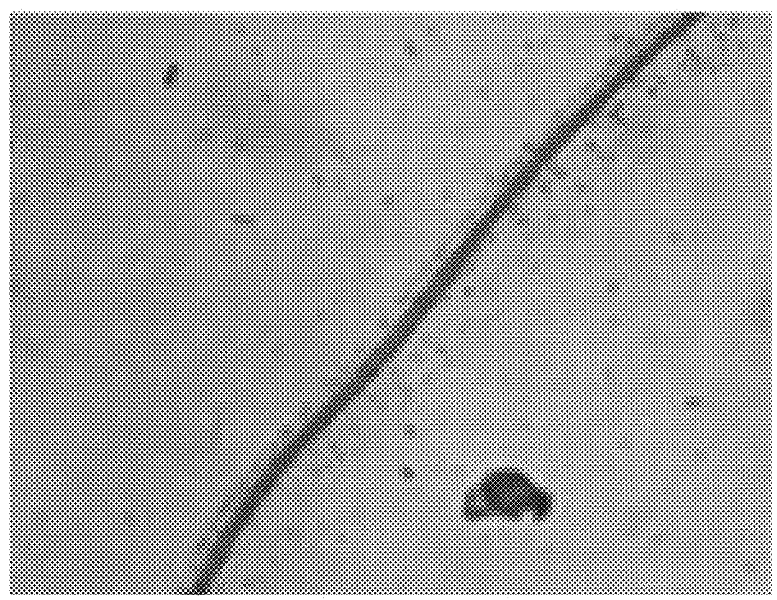
Figure 53:
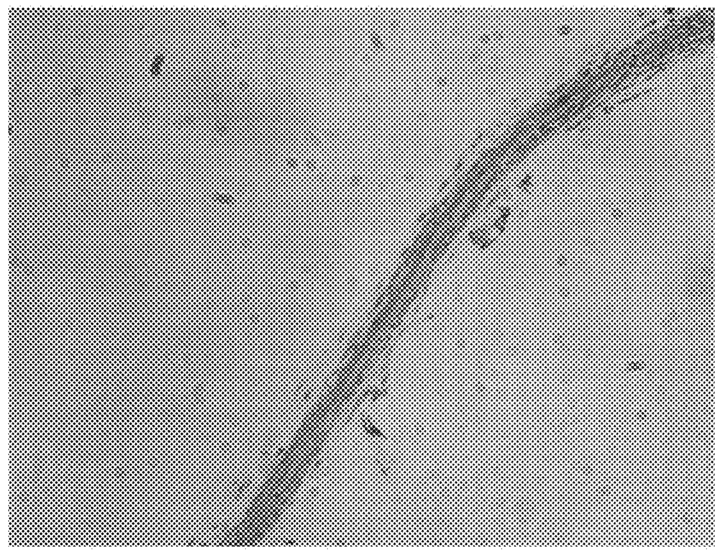
Figure 54:
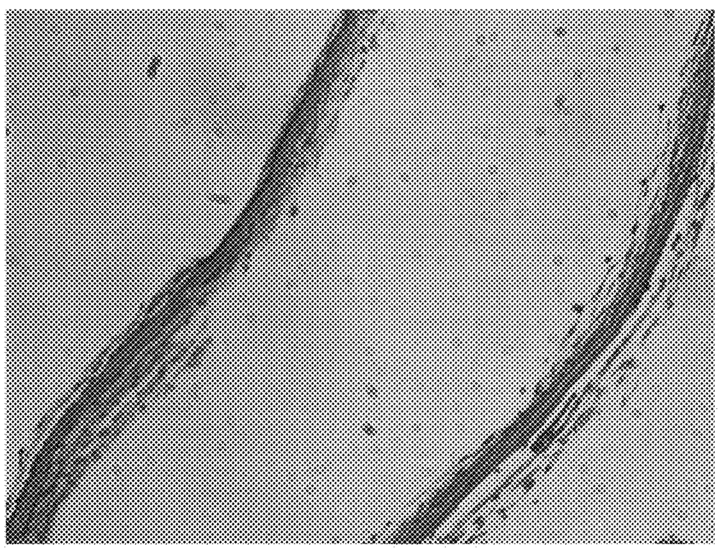

Grids were added to wells and media was prepared to culture 4 wells per group with 1 ml of BGJ growth media per well. As illustrated in FIG. 2, 5 ml of the prepared media 20 was added into each well 22 and fresh cut calvaria 24 were placed on the grid 26. The down selected compounds were examined at various concentrations and a number of positive and negative controls were tested as well. Table 4 illustrates 42 of the 117 samples examined and lists the compounds and concentrations tested for these 42 samples. Media was changed after 24 hours, for a 4 day assays and at 24 hours and 72 hours for a 7 day assays. The new media was added into new plates and the grids with the calvaria bones were transferred into the new wells and the lids were also switched. After 4 days or 7 days calvaria from each group were placed together in 10% buffered formalin and fixed for 24 hours. The calvaria were decalcified for 8 hours and embedded in paraffin blocks for sectioning and histomorphometry. FIGS. 3 through 45 illustrate histologic specimens of the calvaria culture sections for the compounds tested in Table 4 below.

TABLE 4

Histology of Compound and Compound Concentration.

| Figure number | Treatment | Concentration (μM) |
|---|---|---|
| 3 | Negative Control | — |
| 4 | Lovastatin (Positive Control) | 10 |
| 5 | Apomorphine | 1 |
| 6 | Apomorphine | 5 |
| 7 | Apomorphine | 10 |
| 8 | Auranofin | 1 |
| 9 | Auranofin | 5 |
| 10 | Auranofin | 10 |
| 11 | Lomofungin | 1 |
| 12 | Lomofungin | 5 |
| 13 | Lomofungin | 10 |
| 14 | N-Butyldeoxynojirimcyin | 1 |
| 15 | N-Butyldeoxynojirimcyin | 5 |
| 16 | N-Butyldeoxynojirimcyin | 10 |
| 17 | Negative Control | — |
| 18 | PS-1 (Positive Control) | 1 |
| 19 | Quinacrine | 1 |
| 20 | Quinacrine | 5 |
| 21 | Quinacrine | 10 |
| 22 | Terfenadine | 1 |
| 23 | Terfenadine | 5 |
| 24 | Terfenadine | 10 |
| 25 | Astemizole | 1 |
| 26 | Astemizole | 5 |
| 27 | Astemizole | 10 |
| 28 | Debrisoquinin sulfate | 1 |
| 29 | Debrisoquinin sulfate | 5 |
| 30 | Debrisoquinin sulfate | 10 |
| 31 | Negative control | — |
| 32 | Lovastatin | 10 |
| 33 | Promethazine | 5 |
| 34 | Promethazine | 10 |
| 35 | Promethazine | 20 |
| 36 | Lomofungin | 1 |
| 37 | Lomofungin | 5 |
| 38 | Lomofungin | 10 |
| 39 | n-butyldeoxynojirmycin | 1 |
| 40 | n-butyldeoxynojirmycin | 5 |
| 41 | Control | — |
| 42 | PS-1 | 1 |
| 43 | Quinacrine | 1 |
| 44 | Quinacrine | 5 |
| 45 | Quinacrine | 10 |
| 46 | Terfenadine | 10 |
| 47 | Astemizole | 1 |
| 48 | Astemizole | 5 |
| 49 | Astemizole | 10 |
| 50 | Debrisoquinin sulfate | 10 |
| 51 | control | — |
| 52 | Lovastatin | 10 |
| 53 | Promethazine | 5 |
| 54 | Promethazine | 10 |

Upon visual analysis, the compounds set forth in Table 5 were identified qualitatively as having a clear effect on BMP-2 gene expression. Specifically, these histological samples illustrate increased osteoblast proliferation, differentiation of osteoblast precursors and bone growth, which is represented by an increased number of cells on the surface of the tissue.

TABLE 5

Compounds Found to Up-Regulate BMP-2 Gene Expression.

Prazosin

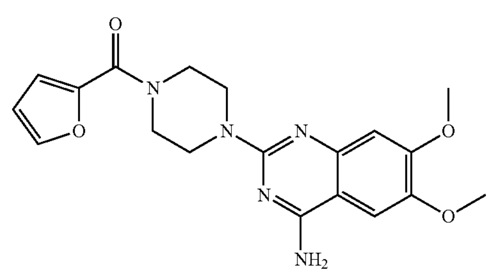 [SMILES: COc1cc2nc(N3CCN(C(=O)c4ccco4)CC3)nc(N)c2cc1OC]

TABLE 5-continued
| Compounds Found to Up-Regulate BMP-2 Gene Expression. | |
|---|---|
| Quinacrine | 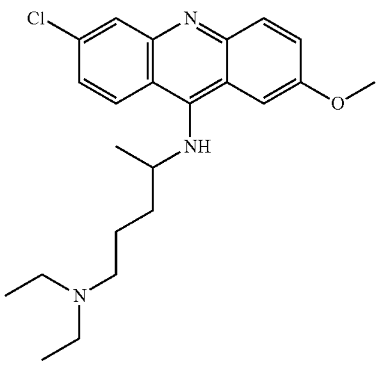 [SMILES: CCN(CC)CCCC(C)Nc1c2ccc(Cl)cc2nc2ccc(OC)cc12] |
| Emetine | 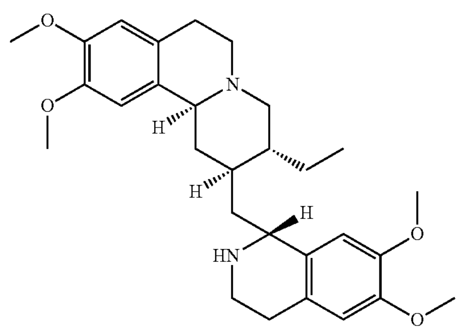 |
| Promethazine | 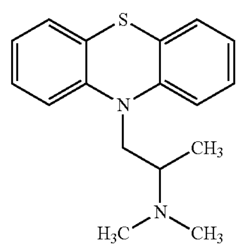 [SMILES: CC(CN1c2ccccc2Sc2ccccc21)N(C)C] |
| Apomorphine | 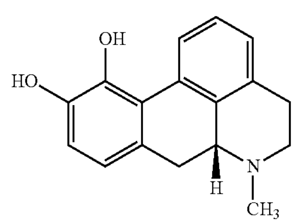 [SMILES: CN1CCc2cccc3c2[C@H]1Cc1ccc(O)c(O)c1-3] |
| Debrizoquine | 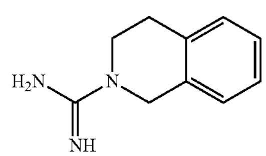 [SMILES: N=C(N)N1CCc2ccccc2C1] |

TABLE 5-continued

| Compounds Found to Up-Regulate BMP-2 Gene Expression. | |
|---|---|
| Terfenadine | 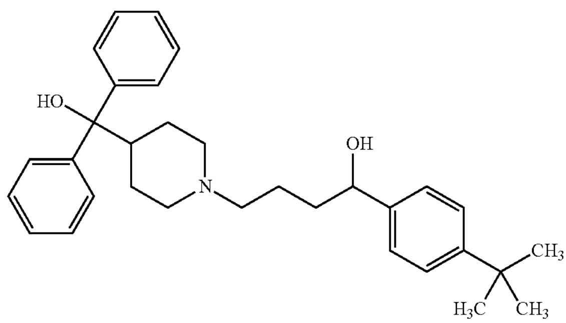 [SMILES: CC(C)(C)c1ccc(C(O)CCCN2CCC(C(O)(c3ccccc3)c3ccccc3)CC2)cc1] |

Study II:
Real Time PCR of Anti-Histaminic Compounds and BMP-2, BMP-4 and BMP-7 Up-Regulation BMP-2, BMP-4 and BMP-47 up-regulation in mesenchymal stem cells was determined for the anti-histaminic $H_1$ receptor compounds listed in Table 6. The testing procedure follows.

TABLE 6

Listing of compounds and doses tested
RNA Extraction

| Compound | Dose | Tube # |
|---|---|---|
| Control | 0 | 1 |
| Control | 0 | 2 |
| Chlorphenamine | 3.5 uM | 3 |
| Chlorphenamine | 3.5 uM | 4 |
| Chlorphenamine | 7 uM | 5 |
| Chlorphenamine | 7 uM | 6 |
| Astemizole | 2.5 uM | 7 |
| Astemizole | 2.5 uM | 8 |
| *Astemizole | 5 uM | 9 |
| *Astemizole | 10 uM | 10 |
| Carebastine | 2.5 uM | 11 |
| Carebastine | 2.5 uM | 12 |
| Carebastine | 5 uM | 13 |
| Carebastine | 5 uM | 14 |
| Carebastine | 10 uM | 15 |
| Carebastine | 10 uM | 16 |
| Ebastine | 2.5 uM | 17 |
| Ebastine | 2.5 uM | 18 |
| Ebastine | 5 uM | 19 |
| Ebastine | 5 uM | 20 |
| *Ebastine | 10 uM | 21 |
| Fexofenadine | 2.5 uM | 22 |
| Fexofenadine | 2.5 uM | 23 |
| Fexofenadine | 5 uM | 24 |
| Fexofenadine | 5 uM | 25 |
| Fexofenadine | 10 uM | 26 |
| Fexofenadine | 10 uM | 27 |
| *Quinacrine | 2.5 uM | 28 |
| *Quinacrine | 5 uM | 29 |
| *Quinacrine | 10 uM | 30 |
| Pheniramine | 2.5 uM | 31 |
| Pheniramine | 2.5 uM | 32 |
| Pheniramine | 5 uM | 33 |
| Pheniramine | 5 uM | 34 |
| Pheniramine | 10 uM | 35 |
| Pheniramine | 10 uM | 36 |
| Terfenadine | 2.5 uM | 37 |
| Terfenadine | 2.5 uM | 38 |
| Terfenadine | 5 uM | 39 |
| Terfenadine | 5 uM | 40 |
| Terfenadine | 10 uM | 41 |
| Terfenadine | 10 uM | 42 |

*Dose caused cell death. Duplicate tubes were combined into one tube for RNA Extraction Cells based assays are done using 6 wells tissue culture plates, seeded with human mesenchymal stem cells (MSC) from Lonza, culture at 80% density. After seeding cells are treated with selected compounds at 10 μM, 5 μM and 2.5 μM for a 24 hour period, mRNA is collected using Qiagen kit RNAeasy kit and cDNA is prepared with same Qiagen kit, RT-PCR is done using kit from SABiosciences to measure gene expression for BMP2, 4 and 7 and run in Applied Biosystems Step One Plus. The protocol for mRNA isolation is described below.

Human mesenchymal stem cell growth medium passage 3 plated in a 6 well plate at 2.5×105 cells/well in hMSC Basal Medium+BulletKit (50 ml Growth Supplement, 10 ml L-Glutamine and 0.5 ml Gentamicin Sulfate Amphotericin-B) for 24 hrs. The compounds to be tested were added and after 24 hrs the media was aspirated, rinsed well once with PBS, and aspirated again. 350 ul of Lysis Buffer was added and the cells were stored at −20° C.

The lysate was homogenized by pipetting the lysate directly into a QIA shredder spin column placed in a 2-mL collection tube, and centrifuge for 2 min at full speed. 70% ethanol was added (1 vol. or 2 ml total) to the homogenized lysate (now at the bottom of the collection tube), and mixed well by pipetting. Up to 700 μL of the sample was transferred, including any precipitate that may have formed, to an RNeasy spin column placed in a 2-mL collection tube. This was centrifuged for 15 seconds at full speed. 700 μL of Buffer RW1 was added to the RNeasy spin column. This was centrifuged for 15 seconds at full speed to wash the spin column membrane.

500 μL of Buffer RPE was added to the RNeasy spin column and centrifuged for 15 seconds at full speed. The flow through was discarded. 500 μL of Buffer RPE was added to the RNeasy spin column and centrifuged for 2 minutes at full speed to wash the spin column membrane. The RNeasy spin column was removed from the collection tube and the flow-through was discarded.

The RNeasy spin column was placed in a new 2-mL collection tube and centrifuged for 1 minute at full speed. The RNeasy spin column was removed from the collection tube, and the flow-through was discarded. The RNeasy spin column was placed in a new 1.5-mL collection tube. 30-50 μL of RNase-free water was added directly to the spin column membrane and this was centrifuged for 1 minute at full speed to elute the RNA.

FIGS. 55-58 illustrate the test results as a chart of control groups versus the fold change exhibited during PCR. Table 7 lists the compounds and dosages for each figure.

TABLE 7

Figure 55:
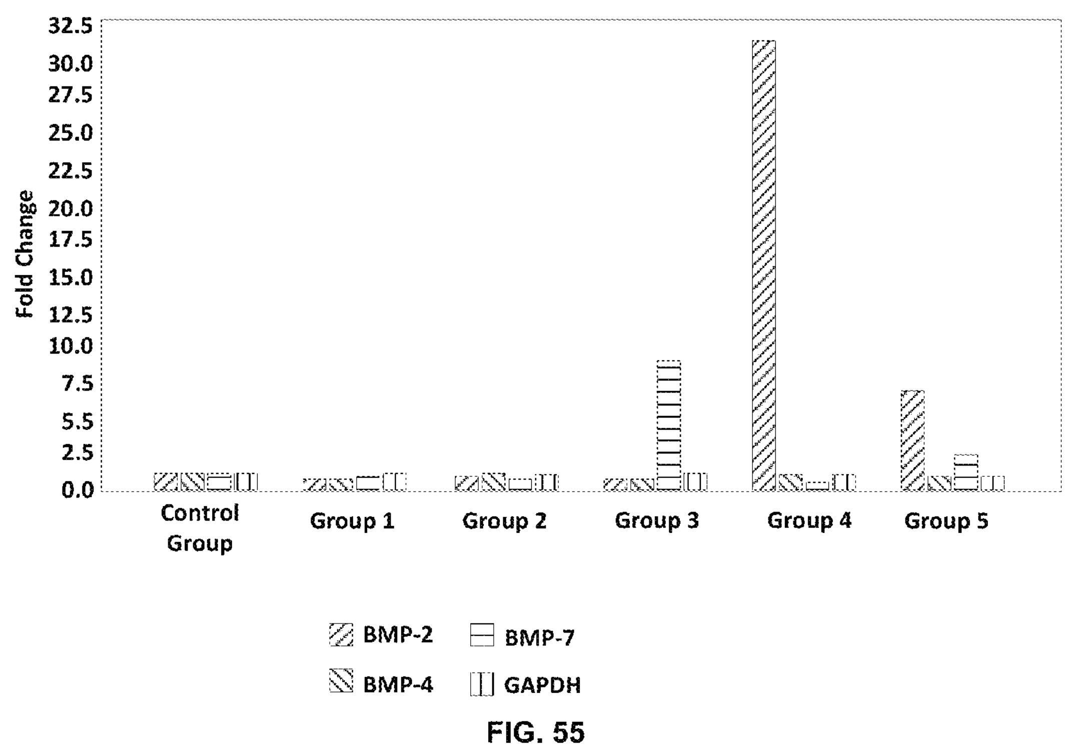
FIGS. 55 through 58 illustrate the fold change of BMP-2, BMP-4 and BMP-7 upon administration of various $H_1$ receptor antagonists.
Figure 56:
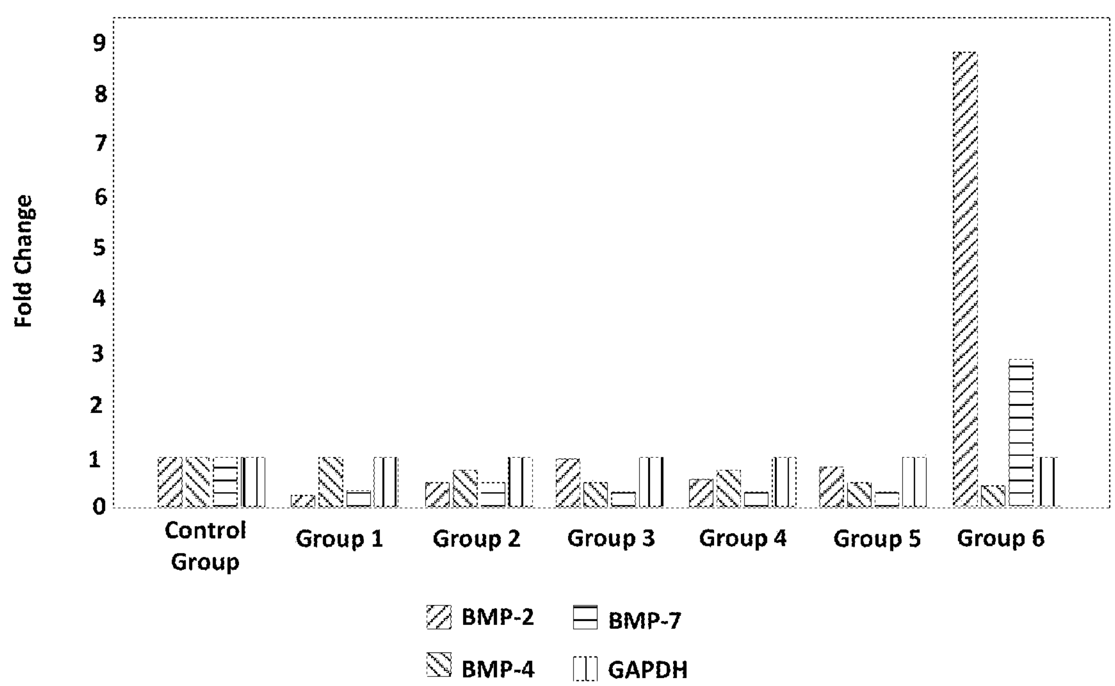
Figure 57:
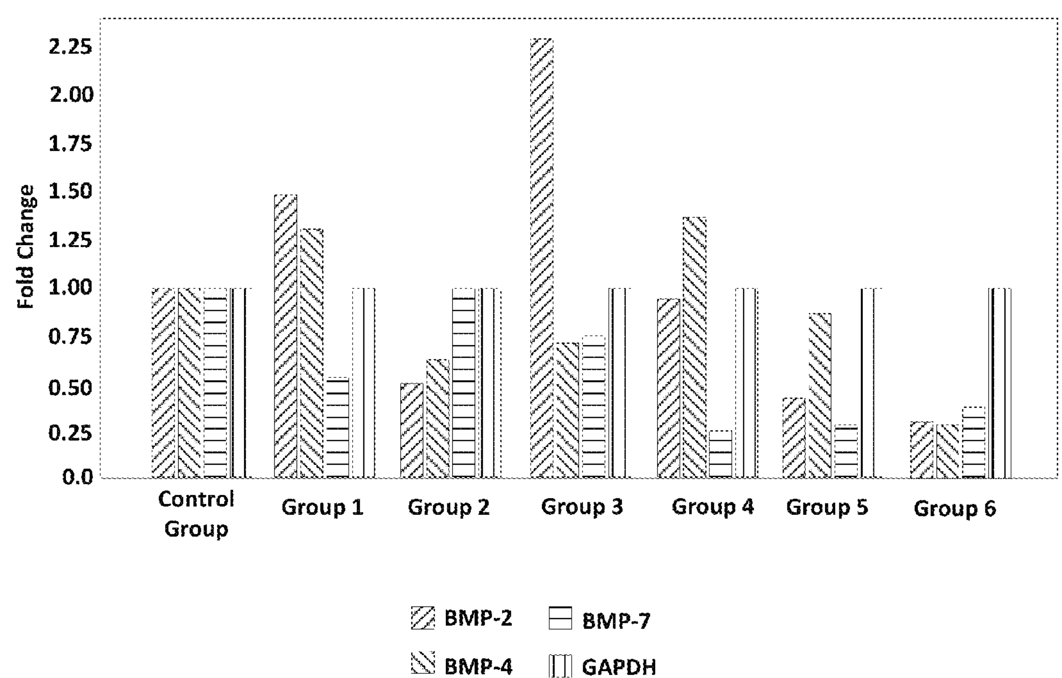
Figure 58:
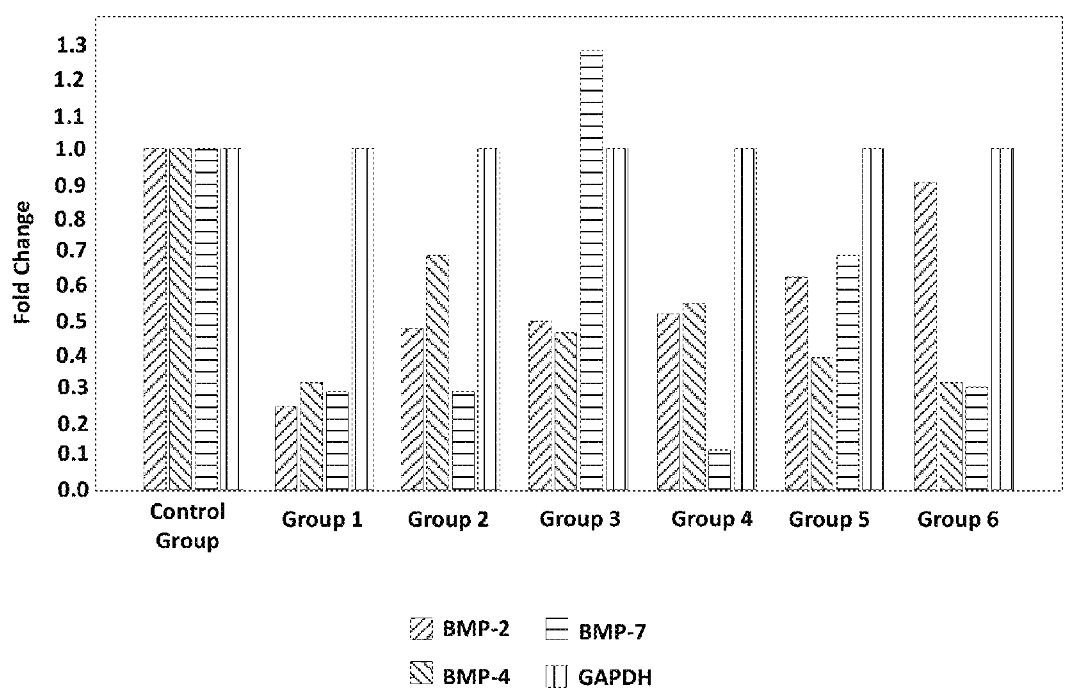
Figure 59:
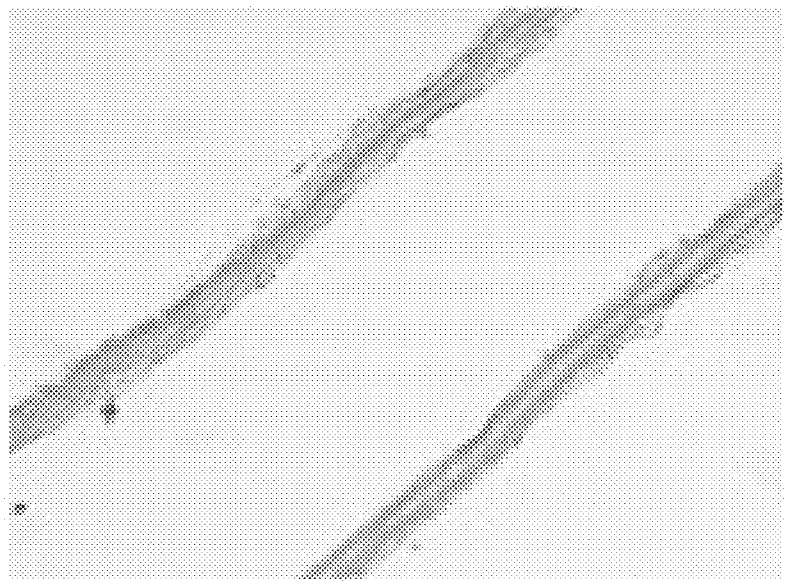
FIGS. 59 through 71 illustrate histological images of murine calvaria samples after treatment.
Figure 60:
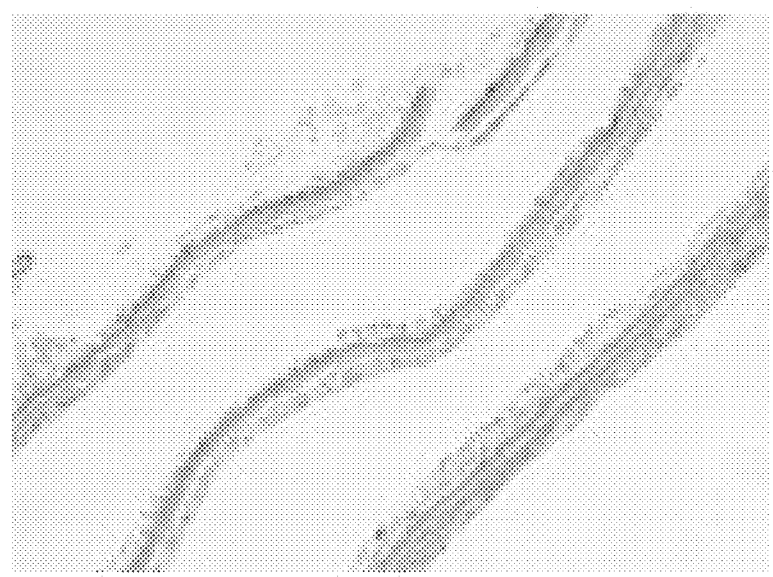
Figure 61:
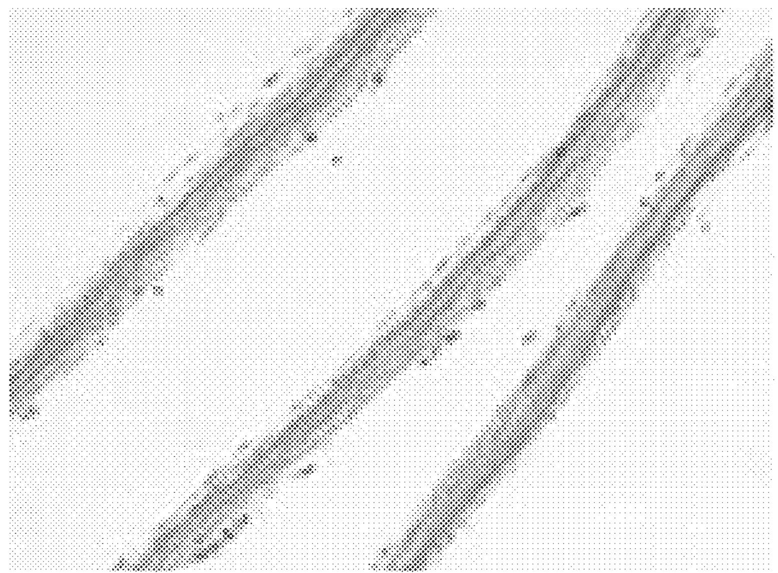
Figure 62:
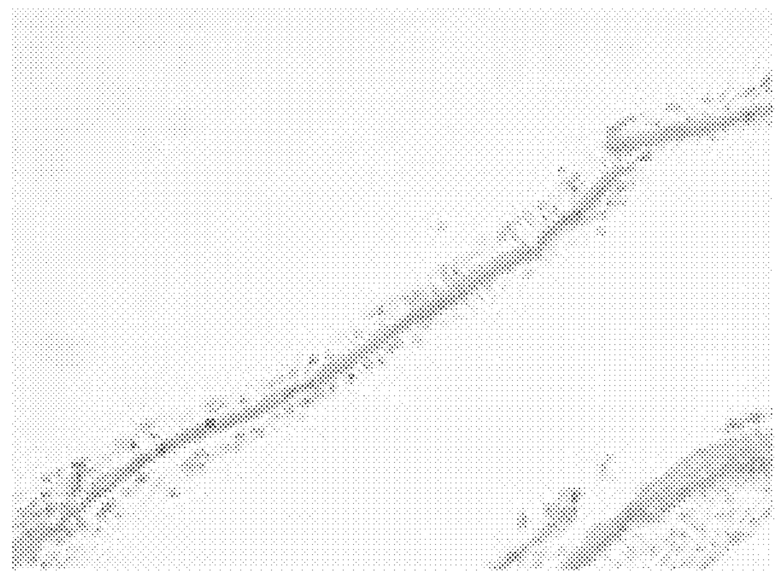
Figures 63, 64:
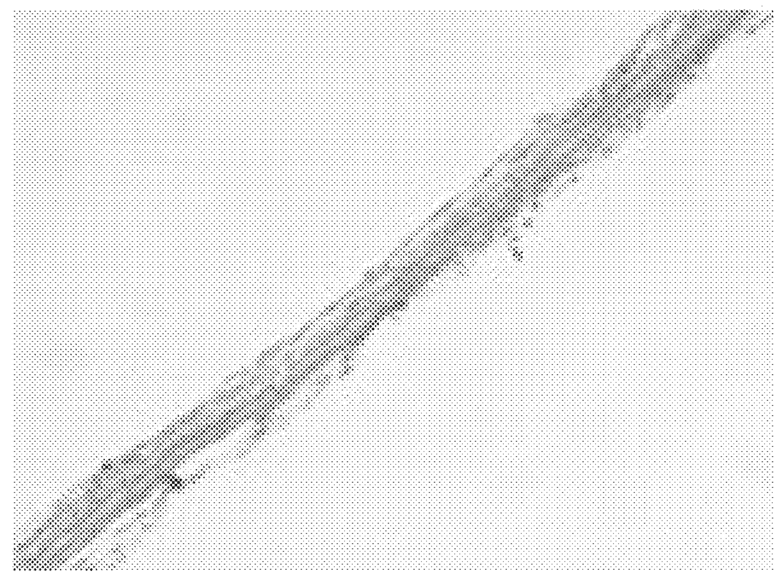
Figure 65:
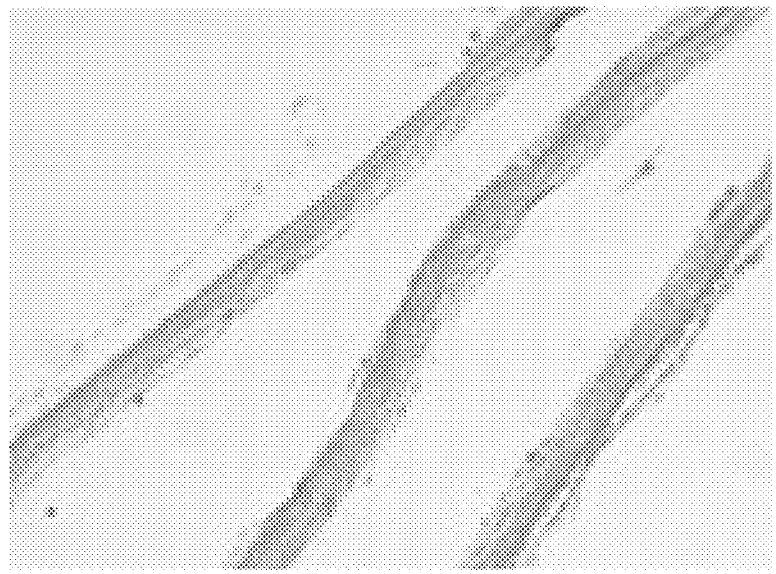
Figure 66:
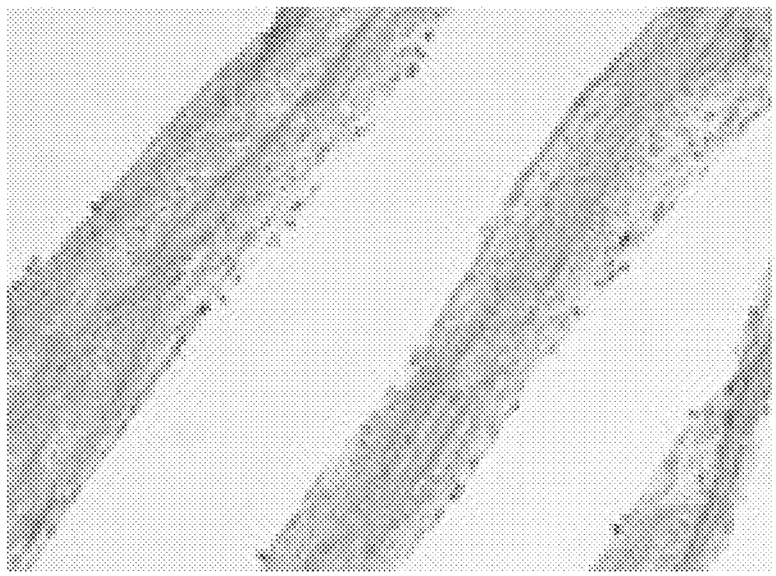
Figure 67:
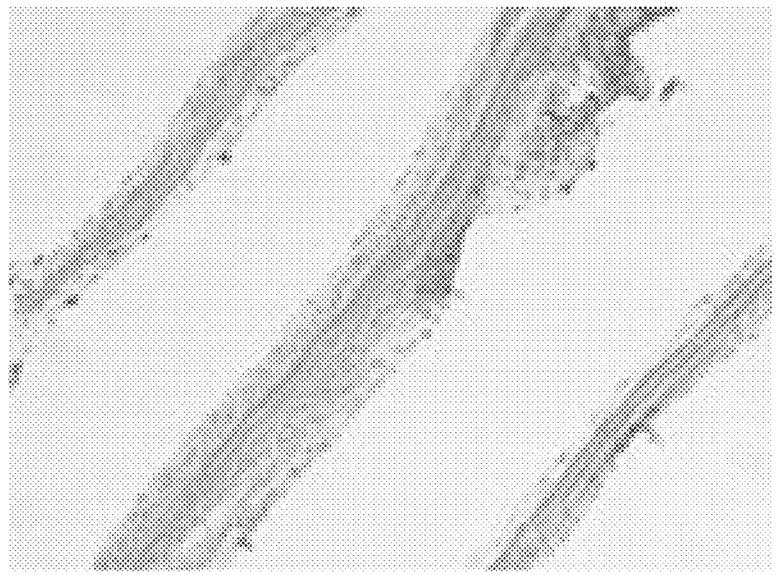
Figure 68:
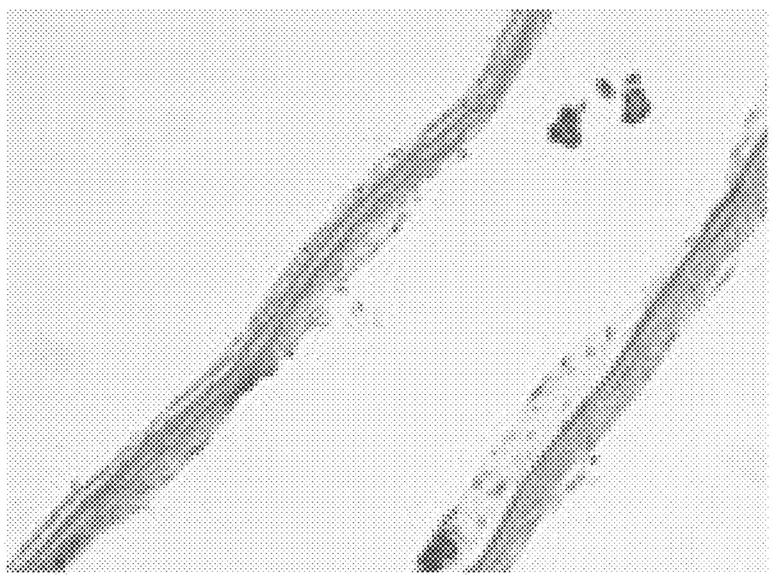
Figures 69, 70:
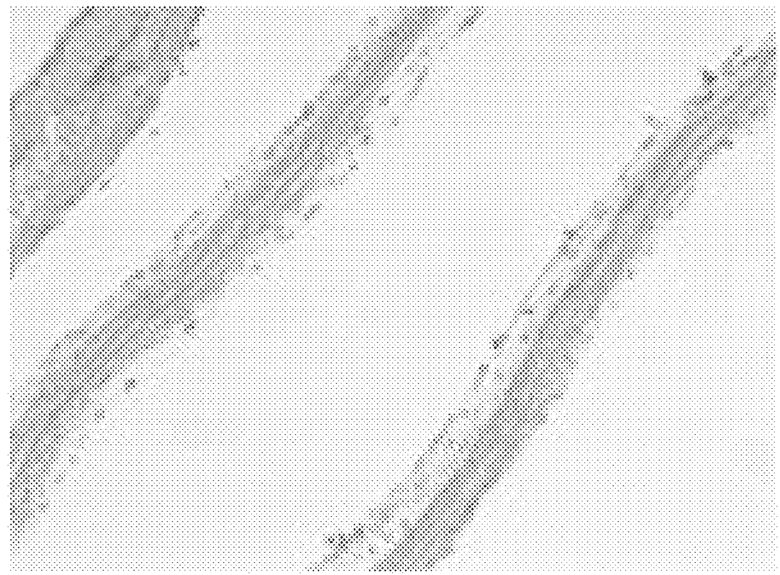
Figure 71:
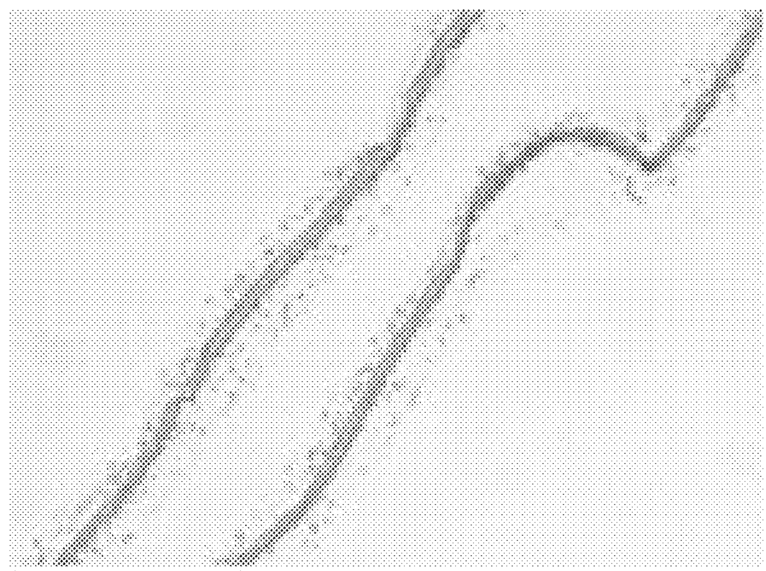

| Effective drugs and dose. | | |
|---|---|---|
| | Compound | Dosage (μM) |
| FIG. 55 | | |
| Control | Control | 0.0 |
| Group 1 | Chlorphenamine | 3.5 |
| Group 2 | Chlorphenamine | 7.0 |
| Group 3 | Astemizole | 2.5 |
| Group 4 | Astemizole | 5.0 |
| Group 5 | Astemizole | 10.0 |
| FIG. 56 | | |
| Control | Control | 0.0 |
| Group 1 | Carebastine | 2.5 |
| Group 2 | Carebastine | 5.0 |
| Group 3 | Carebastine | 10. |
| Group 4 | Ebastine | 2.5 |
| Group 5 | Ebastine | 5.0 |
| Group 6 | Ebastine | 10.0 |
| FIG. 57 | | |
| Control | Control | 0.0 |
| Group 1 | Pheniramine | 2.5 |
| Group 2 | Pheniramine | 5.0 |
| Group 3 | Pheniramine | 10.0 |
| Group 4 | Terfenadine | 2.5 |
| Group 5 | Terfenadine | 5.0 |
| Group 6 | Terfenadine | 10.0 |
| FIG. 58 | | |
| Control | Control | 0.0 |
| Group 1 | Fexofenadine | 2.5 |
| Group 2 | Fexofenadine | 5.0 |
| Group 3 | Fexofenadine | 10.0 |
| Group 4 | Ebastine | 2.5 |
| Group 5 | Ebastine | 5.0 |
| Group 6 | Ebastine | 10.0 |

The resultant effective drugs and dosages are summarized below in Table 8. As seen below, astemizole, ebastine and pheniramine were found to exhibit BMP-2 fold increases. In addition, astemizole and ebastine were found to exhibit BMP-7 fold increases. However, fold increases were not observed for BMP-4. It is noted that carebastine is an active carboxylic acid metabolite of ebastine.

TABLE 8

| Effective drugs and dose. | | | |
|---|---|---|---|
| Compound | BMP-2 Fold Increase/Dose | BMP-4 Fold Increase/Dose | BMP-7 Fold Increase/Dose |
| 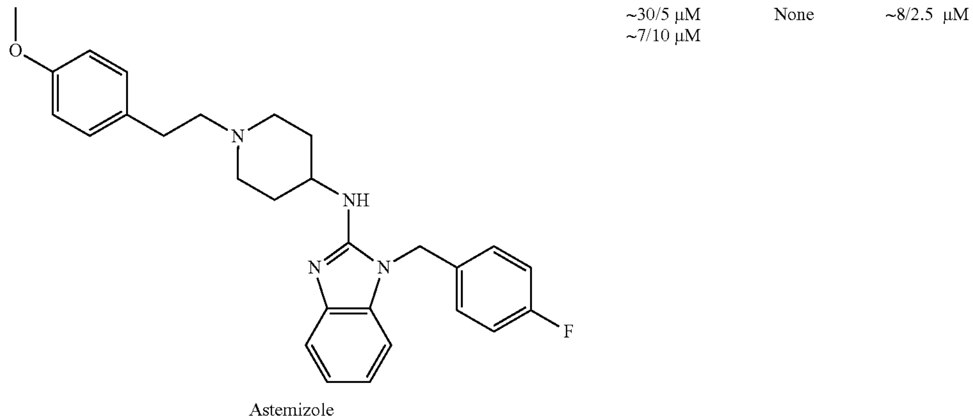<br>Astemizole | ~30/5 μM<br>~7/10 μM | None | ~8/2.5 μM |
| 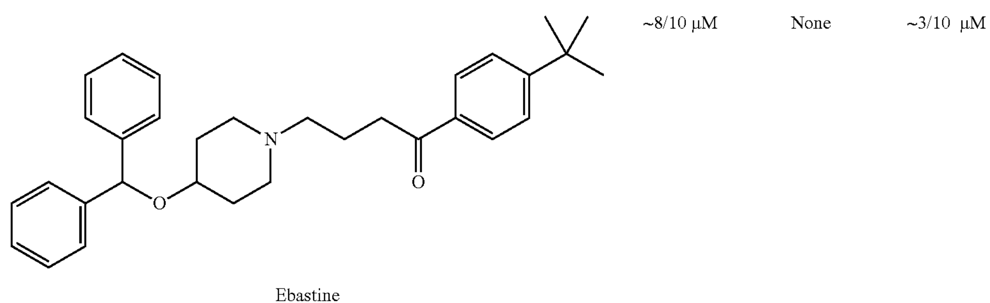<br>Ebastine | ~8/10 μM | None | ~3/10 μM |

TABLE 8-continued

| Effective drugs and dose. | | | |
|---|---|---|---|
| Compound | BMP-2 Fold Increase/Dose | BMP-4 Fold Increase/Dose | BMP-7 Fold Increase/Dose |
| 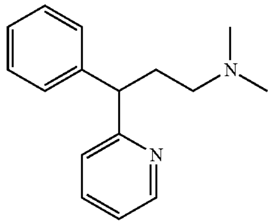 [SMILES: CN(C)CCC(c1ccccc1)c1ccccn1] Pheniramine | ~2/10 μM | None | None |

Anabolic Assays Using Murine Calvaria

To investigate the biological effects on bone of the compounds from the PCR assays a number of assays were performed using murine calvaria bone as follows. Following procedures similar to those outlined above in Study I, murine calvaria bone was removed from 4 day old pups form CD-1 time pregnant mice from Harlan (15 day gestation at time of arrival). The pups were decapitated with scissors after dipping the pups in 95% ethanol. The scalp was then removed. The heads were placed in a Petri dish with BGJ medium. The calvaria bones were cut using curved scissors to make a cut along the suture of the calvaria bone and the two parts were carefully removed from the brain. The calvaria were trimmed avoiding the suture area. The collected tissue was placed into media (3 bones per group) including BGJ+L-Glutamine with 1% Pen/Strep and 1% BSA. The dish including the bones was placed into a 37° C. and 5% $CO_2$ incubator.

The selected compounds were prepared in a solution of dimethyl sulfoxide (DMSO) to form stock solutions of each compound, with the exception of terfenadine, which was prepared in ethanol. Specifically, a 10 mM stock solution was prepared for PS1, a 25 mM stock solution was prepared for carebastine and a 50 mM stock solution was prepared for ebastine, #6 terfenadine, fexofenadine and astemizole. The concentrations of the solutions were then adjusted by adding the stock composition to BGJ media with 25 mg/ml of L-ascorbic acid. Table 9 describes the compounds utilized in each experimental group, which were mixed with BGJ media with 25 mg/ml L-ascorbic acid, and the corresponding histological figure obtained using the histological studies described further below.

TABLE 9

Compounds and doses tested

| Group | Compound | Dose | Figure |
|---|---|---|---|
| Group 1 | Control | — | 59 |
| Group 2 | PSI | 0.1 μM | 60 |
| Group 3 | Ebastine | 5 μM | 61 |
| Group 4 | Ebastine | 10 μM | 62 |
| Group 5 | Ebastine | 20 μM | 63 |
| Group 6 | Carebastine | 5 μM | 64 |
| Group 7 | Carebastine | 10 μM | 65 |
| Group 8 | Carebastine | 20 μM | 66 |
| Group 9 | Control | — | |
| Group 10 | Terfenadine | 5 μM | 67 |
| Group 11 | Fexofenadine | 10 μM | 68 |

TABLE 9-continued

Compounds and doses tested

| Group | Compound | Dose | Figure |
|---|---|---|---|
| Group 12 | Fexofenadine | 20 μM | 69 |
| Group 13 | Astemizole | 10 μM | 70 |
| Group 14 | Astemizole | 20 μM | 71 |

To prepare the 10 mM stock solution of PS1, 1 mg of PS1 having a molecular weight of 618.8 was added to 162 μl of DMSO. For preparing the 50 mM stock solution of ebastine, 10 mg of ebastine having a molecular weight of 469.66 was added to 426 μl of DMSO. In preparing the 25 mM solution of carebastine, 1 mg of carebastine having a molecular weight of 499.65 was added to 80μ of DMSO. To obtain the 50 mM terfenadine stock solution 1.5 mg of terfenadine having a molecular weight of 471.7 was added to 64 μl of ETOH. To prepare the 50 mM stock solution of fexofenadine, 10 mg of fexofenadine chloride having a molecular weight of 538.12 was added to 372 μl of DMSO. Further, to prepare the 50 mM stock solution of astemizole, 10 mg of astemizole having a molecular weight of 458.57 was added to 436 μl of DMSO. Table 10 then lists the preparation of the solutions for use in the tests above.

TABLE 10

Preparation of the Solutions Used Above from the Stock Solutions

| | | |
|---|---|---|
| PS1 Stock @ 10 mM | 5 μl of 10 mM/100 μl CD = 0.5 mM | 2 ul of .5 mM in 10 ml of media |
| Ebastine Stock @ 50 mM | 10 μl of 50 mM/100 μl CD = 5 mM | 28 μl of 5 mM in 7 ml of media = 20 μM → 1:2 |
| Carebastine Stock @ 25 mM | 10 μl of 25 mM/100 μl CD = 2.5 mM | 56 μl of 2.5 mM in 7 ml of media = 20 μM → 1:2 |
| #6 Terfenadine Stock @ 50 mM | 10 ul of 50 mM/100 ul CD = 5 mM | 5 ul of 5 mM in 5 ml media = 5 uM |
| Fexofenadine Stock @ 50 mM | 10 ul of 50 mM/100 ul CD = 5 mM | Use 22 ul of 5 mM in 5.5 ml of media = 20 uM → 1:2 |
| Astemizole Stock @ 50 mM | 10 ul of 50 mM/100 ul CD = 5 mM | Use 22 ul of 5 mM in 5.5 ml of media = 20 uM → 1:2 |

The prepared media, including the compounds of interest, was added to culture plate wells including the fresh cut calvaria placed on grids within the wells. A control group was set up for each carrier. The calvariam were collected from all groups on day 4 and day 7 and placed in a 10% buffered formalin and fixed for 24 hours. The calvariam were decalcified in 10% EDTA for 8 hours. After decalcification, the calvariam are processed in an automated tissue processor programmed for neonatal mouse calvariam, embedded in paraffin blocks, and sectioned.

The staining procedure was as follows: Xylene 3×2 minutes; 100% Ethanol 3×1 minute; 95% Ethanol 1×1 minute; 80% Ethanol 1×1 minute; Water 1×3 minutes; Hematoxylin 1×30 seconds; Water change until rinse water is clear; 0.5% w/v aqueous ammonia 1×10 seconds; Water 1×3 minutes; 80% ethanol 1×1 minute; 95% ethanol 1×1 minute; Eosin 1×2 minutes; 95% ethanol 3×1 minute; 100% ethanol 3×1 minute; Xylene 3×1 minute and coverslip with permount.

Optical microscopy was utilized for analysis at 10× magnification. Upon visual analysis, the compounds set forth in Table 11 were identified qualitatively as having a clear effect on BMP-2 gene expression and the histological samples illustrate increased osteoblast proliferation, differentiation of osteoblast precursors and bone growth, which is represented by an increased number of cells on the surface of the tissue.

It is noted that while carebastine did not exhibit a fold change of greater than 1, the histological specimens illustrate that carebastine was relatively active in the bone calvaria assay.

TABLE 11

Compounds identified as having an effect on BMP-2 gene expression

| Compound | Formula |
|---|---|
| Ebastine | |
| Pheniramine | |
| Carebastine | $CH_3$, COOH, $CH_3$, N, O |
| Astemizole | |

TABLE 11-continued

| Compounds identified as having an effect on BMP-2 gene expression | |
|---|---|
| Compound | Formula |
| Terfenadine | 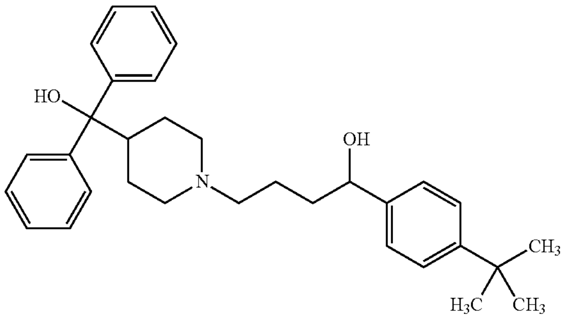 [SMILES: CC(C)(C)c1ccc(C(O)CCCN2CCC(C(O)(c3ccccc3)c3ccccc3)CC2)cc1]  |

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

What is claimed is:

1. A method of treating a bone defect in a subject, which method comprises administering by parenteral administration to a subject suffering a bone fracture or having a post-plastic bone surgery an amount of 0.2 to 40 mg/kg/day of a composition comprising carebastine, thereby stimulating up-regulation of endogenous BMP-2 gene expression by at least two folds or increasing bone mass by at least 20% in said subject.

2. The method of claim 1 further comprising administering to said subject one or more additional agents that promote tissue growth or infiltration.

3. The method of claim 2, wherein said one or more additional agents is selected from the group consisting of epidermal growth factors, fibroblast growth factors, platelet-derived growth factors, transforming growth factors, parathyroid hormones, leukemia inhibitory factors, insulin-like growth factors, bone morphogenetic proteins and antiresorptive agents.

4. The method of claim 1, wherein said subject is human.

5. The method of claim 1, wherein said subject is a non-human vertebrate.

6. The method of claim 1, wherein said composition is administered by injection.

7. The method of claim 1, wherein said up-regulation of endogenous BMP-2 gene expression enhances bone formation.

* * * * *